United States Patent
DeLuca et al.

(10) Patent No.: US 6,362,350 B1
(45) Date of Patent: Mar. 26, 2002

(54) CRYSTALLINE 1α, 24(S)-DIHYDROXYVITAMIN $D_2$ AND METHOD OF PURIFICATION THEREOF

(75) Inventors: Hector F. DeLuca, Deerfield; Rafal R. Sicinski, Madison; Hazel Holden, Fitchburg; James Brian Thoden, Madison, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/437,307

(22) Filed: Nov. 10, 1999

Related U.S. Application Data

(60) Provisional application No. 60/141,967, filed on Jul. 1, 1999.

(51) Int. Cl.$^7$ ...................... C07C 401/00; A61K 31/59
(52) U.S. Cl. ...................... 552/653; 514/167
(58) Field of Search ............... 552/653; 514/167

(56) References Cited

U.S. PATENT DOCUMENTS

| | | | |
|---|---|---|---|
| 3,665,020 A | 5/1972 | Marbet | 260/397.2 |
| 4,022,891 A | 5/1977 | Takeshita et al. | 424/236 |
| 4,159,326 A | 6/1979 | Barton et al. | 424/236 |
| 4,670,190 A | 6/1987 | Hesse et al. | 260/397.2 |
| 5,098,899 A | 3/1992 | Gilbert et al. | 514/167 |
| 5,789,397 A | 8/1998 | Bishop et al. | 514/167 |

FOREIGN PATENT DOCUMENTS

| | | |
|---|---|---|
| EP | 0270867 | 6/1988 |
| WO | WO94/05630 | 3/1994 |

OTHER PUBLICATIONS

Strugnell et al "1 β24(S)–Dihydroxyvitamin $D_2$: a biologically active product of 1 β–hydroxyvitamin $D_2$ made in the human hepatoma, Hep3B", Biochemistry Journal, 310, pp. 233–241, 1995.

*Primary Examiner*—Sabiha Qazi
(74) *Attorney, Agent, or Firm*—Andrus, Sceales, Starke & Sawall, LLP

(57) ABSTRACT

A method of purifying 1α,24(S)-dihydroxyvitamin $D_2$ to obtain 1α,24(S)-dihydroxyvitamin $D_2$ in crystalline form. The method includes the steps of boiling a solvent under inert atmosphere, dissolving a product containing 1α,24(S)-dihydroxyvitamin $D_2$ to be purified in the solvent, cooling the solvent and dissolved product below ambient temperature for a sufficient amount of time to form a precipitate of 1α,24(S)-dihydroxyvitamin $D_2$ crystals, and recovering the 1α,24(S)-dihydroxyvitamin $D_2$ crystals. The purification technique involves using one of several binary solvent systems, namely, acetone and hexane, 2-propanol and hexane, or ethyl formate and petroleum ether.

17 Claims, 14 Drawing Sheets

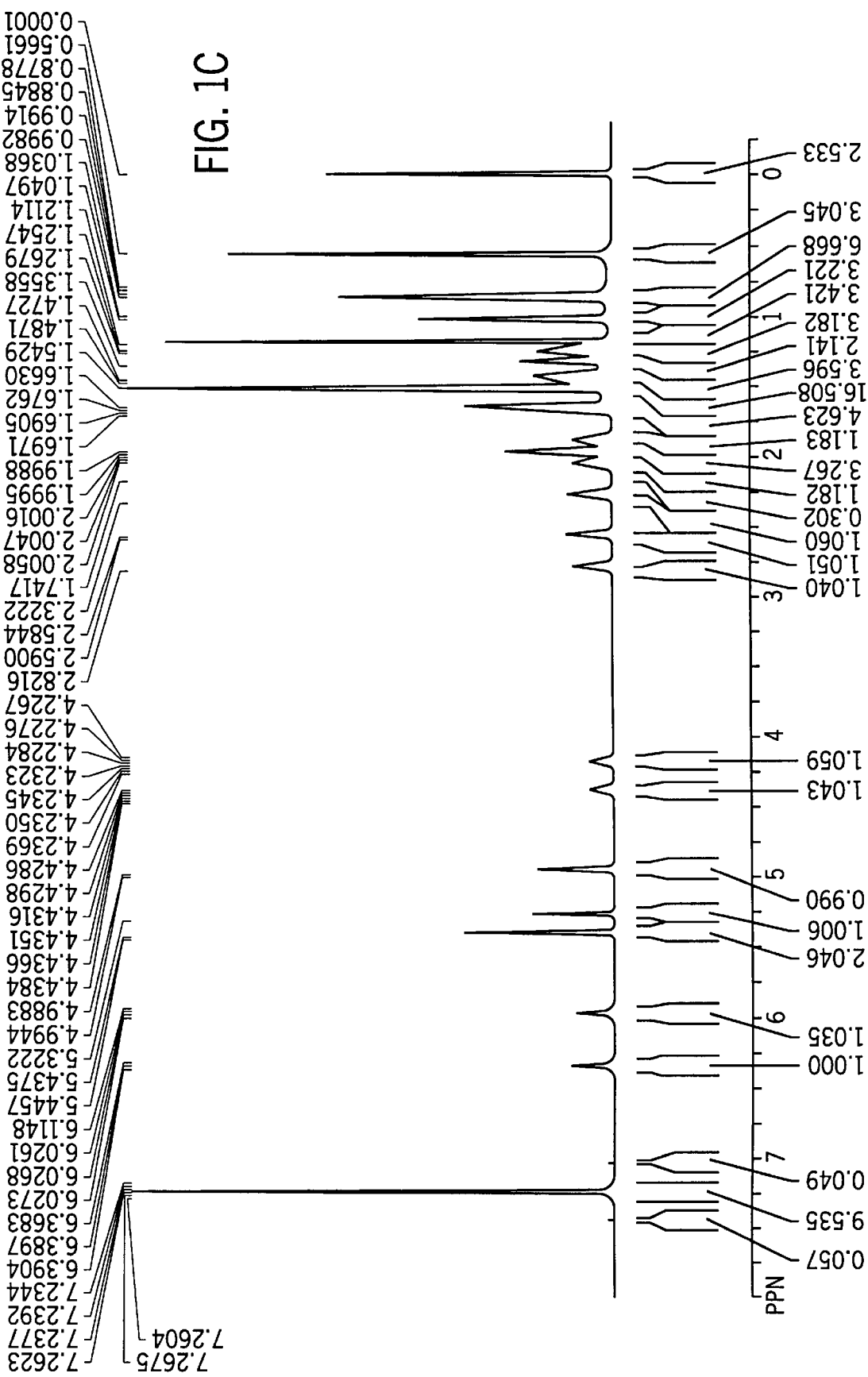

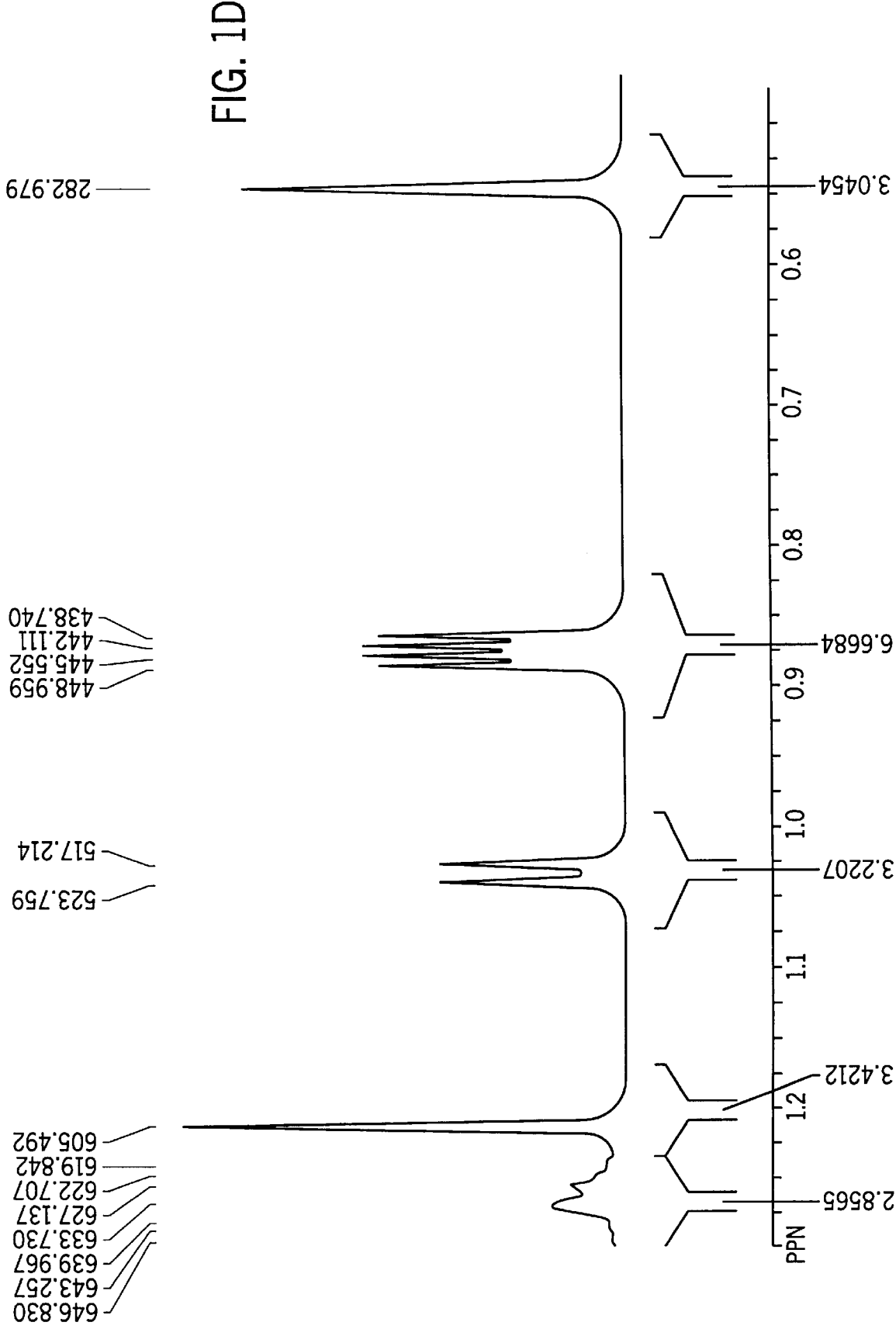

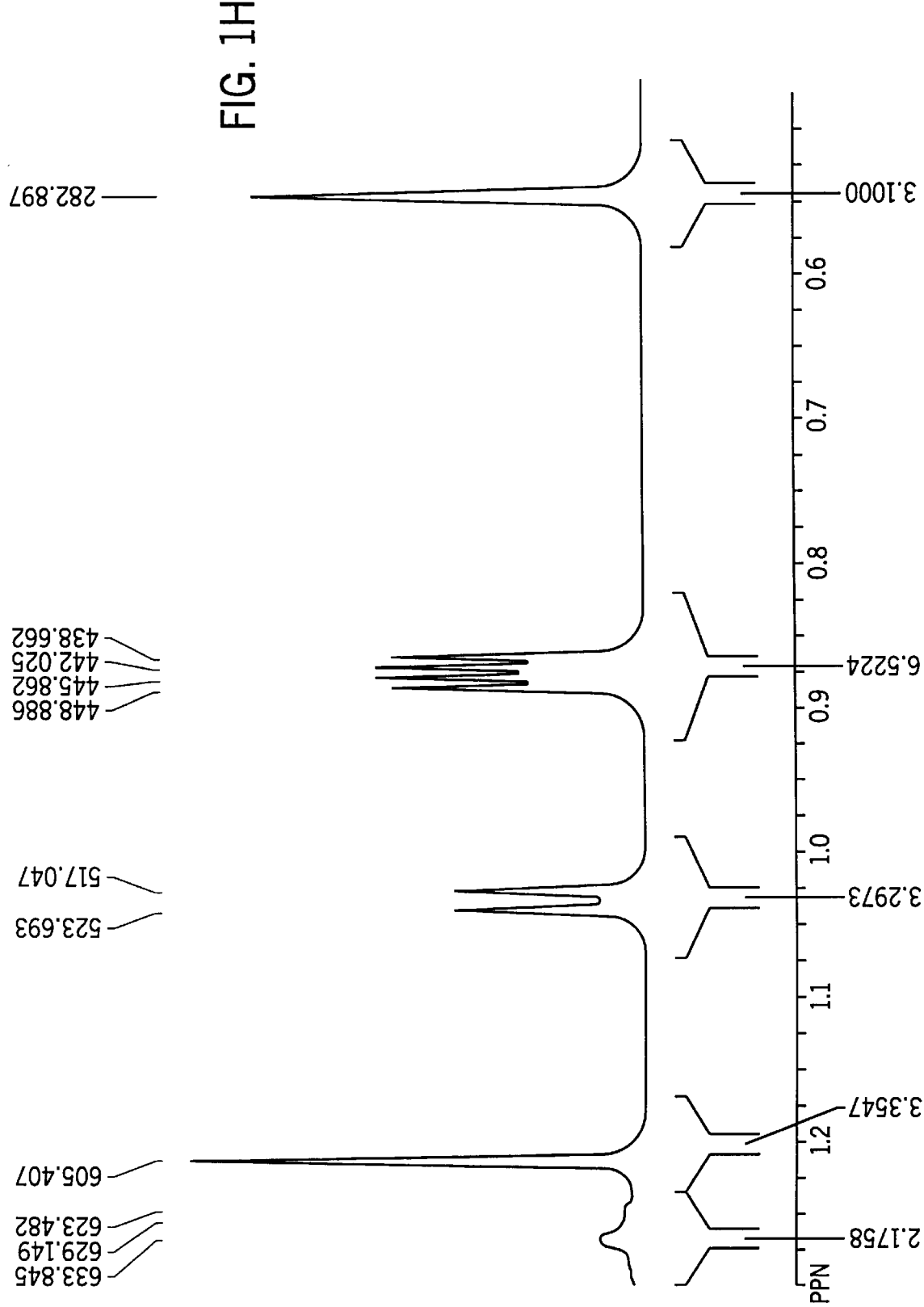

CRYSTALLINE 1α, 24(S)-DIHYDROXYVITAMIN $D_2$ AND METHOD OF PURIFICATION THEREOF

CROSS-REFERENCE TO RELATED APPLICATIONS

This application claims the benefit of U.S. Provisional Application No. 60/141,967, filed Jul. 1, 1999.

BACKGROUND AND SUMMARY OF THE INVENTION

The present invention relates to purification of organic compounds, and more particularly to the purification of a pharmacologically important 1α,24(S)-dihydroxyvitamin $D_2$ compound (1α,24(S)-(OH)$_2D_2$) by preparing it in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of 5,6-trans geometric isomer of vitamin D is performed, followed by SeO$_2$/NMO oxidation and photochemical irradiation [see Andrews et al., *J. Org. Chem.* 51, 1635 (1986); Calverley et al., *Tetrahedron* 43, 4609 (1987); Choudry et al., *J. Org. Chem.* 58, 1496 (1993)], the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the previtamin D compound, followed by cycloreversion of the modified adduct under basic conditions [Nevinckx et al., *Tetrahedron* 47, 9419 (1991); Vanmaele et al., *Tetrahedron* 41, 141 (1985) and 40, 1179 (1991); Vanmaele et al., *Tetrahedron Lett.* 23, 995 (1982)], one can expect that the desired 1α-hydroxyvitamin can be contaminated with the previtamin 5(10),6,8-triene and 1β-hydroxy isomer. One of the most useful C-1 hydroxylation methods, of very broad scope and numerous applications, is the experimentally simple procedure elaborated by Paaren et al. [see *J. Org. Chem.* 45, 3253 (1980) and *Proc. Natl. Acad. Sci. U.S.A.* 75, 2080 (1978)]. This method consists of allylic oxidation of 3,5-cyclovitamin D derivatives, readily obtained from the buffered solvolysis of vitamin D tosylates, with SeO$_2$/t-BuOOH and subsequent acid-catalyzed cycloreversion to the desired 1α-hydroxy compounds. Taking into account this synthetic path it is reasonable to assume that the final product can be contaminated with 1β-hydroxy epimer, 5,6-trans isomer and the previtamin D form.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of the some water-elimination reactions; their driving force is the allylic (1α-) and homoallylic (3β-) position of the hydroxy groups. The presence of such abovementioned oxidation and elimination products can be easily detected by thin-layer chromatography. Thus, for example, using precoated aluminum silica sheets [with UV indicator; from EM Science (Cherry Hill, N.J.)] and solvent system hexane-ethyl acetate (3:7), the spot of 1α,24(S)—(OH)$_2D_2$ ($R_f$ 0.40) and its elimination products ($R_f$'s ca. 0.8–0.9) are visible in ultraviolet light. Also, after spraying with sulfuric acid and heating, an additional spot can be visualized ($R_f$ 0), derived from oxidation products.

Usually, all 1α-hydroxylation procedures require at least one chromatographic purification. However, even chromatographically purified 1α,24(S)-dihydroxyvitamin $D_2$ although showing consistent spectroscopic data, suggesting its homogeneity, does not meet the purity criteria required for therapeutic agents that can be orally, parenterally or transdermally administered. Therefore, it was evident that a suitable method of purification of 1α,24(S)-dihydroxyvitamin $D_2$ is required.

Since it is well known that the simplest procedure that can be used for compound purification is a crystallization process, it has been decided to investigate purification of 1α,24(S)—(OH)$_2D_2$ by means of crystallization. The solvent plays a crucial role in the crystallization process, and is typically an individual liquid substance or a suitable mixture of different liquids. For crystallizing 1α,24(S)-dihydroxyvitamin $D_2$, the most appropriate solvent and/or solvent system is characterized by the following factors:

(1) low toxicity;
(2) low boiling point;
(3) significant dependence of solubility properties with regard to temperature (condition necessary for providing satisfactory crystallization yield); and
(4) relatively low cost.

It is believed that highly apolar solvents (e.g. hydrocarbons) were not suitable due to their low solubility potency. Quite the reverse situation occurred in the highly polar media (e.g. alcohols), in which 1α,24(S)—(OH)$_2D_2$, showed too high solubility. Therefore, it is concluded that for the successful crystallization of 1α,24(S)—(OH)$_2D_2$, a solvent mixture is required, consisting of two (or more) solvents differing considerably in polarity. After numerous experiments, it was found that several binary solvent systems were useful for the crystallization of 1α,24(S)—(OH)$_2D_2$, namely: acetone-hexane, 2-propanol-hexane and ethyl formate-petroleum ether. These solvents are all characterized by low toxicity, and they are very easy to remove by evaporation or other well known methods. In all cases it is believed the crystallization process will occur easily and efficiently, and the precipitated crystals will be sufficiently large to assure their recovery by filtration.

BRIEF DESCRIPTION OF THE DRAWINGS

FIGS. 1*a*–1*h* are graphs of $^1$H NMR spectrum (CDCl$_3$, 500 MHz) of the solid 1α,24(S)-dihydroxyvitamin $D_2$ material before crystallization (FIGS. 1*a* and 1*b*) as well as the spectra of the crystals of 1α,24(S)—(OH)$_2D_2$ which resulted after two crystallizations using the following solvent systems: acetone-hexane (FIGS. 1*c* and 1*d*), 2-propanol-hexane (FIGS. 1*e* and 1*f*) and HCOOEt-petroleum ether (FIGS. 1*g* and 1*h*);

DETAILED DESCRIPTION OF THE INVENTION

The present invention provides a valuable method of purification of 1α,24(S)-dihydroxyvitamin $D_2$, a pharmacologically important compound, characterized by the formula shown below:

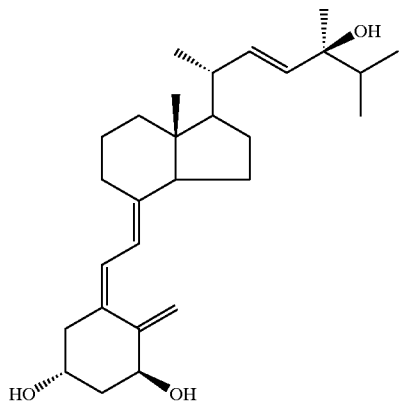

The purification technique involves obtaining the 1α,24(S)-dihydroxyvitamin $D_2$ product in crystalline form by utilizing a crystallization procedure wherein the 1α,24(S)-dihydroxyvitamin $D_2$ material to be purified is dissolved using as the solvent system one of the following:

(1) acetone and hexane;

(2) 2-propanol and hexane; or (3) ethyl formate and petroleum ether.

Thereafter, the solvent or solvent system can be removed by evaporation, with or without vacuum, or via other means as is well known. The technique can be used to purify a wide range of final products containing 1α,24(S)-dihydroxyvitamin $D_2$ obtained from any known synthesis thereof, and in varying concentrations, i.e. from microgram amounts to kilogram amounts. As is well known to those skilled in this art, the amount of solvent utilized should be minimized and/or adjusted according to the amount of 1α,24(S)-dihydroxyvitamin $D_2$ to be purified.

Figure 1A:
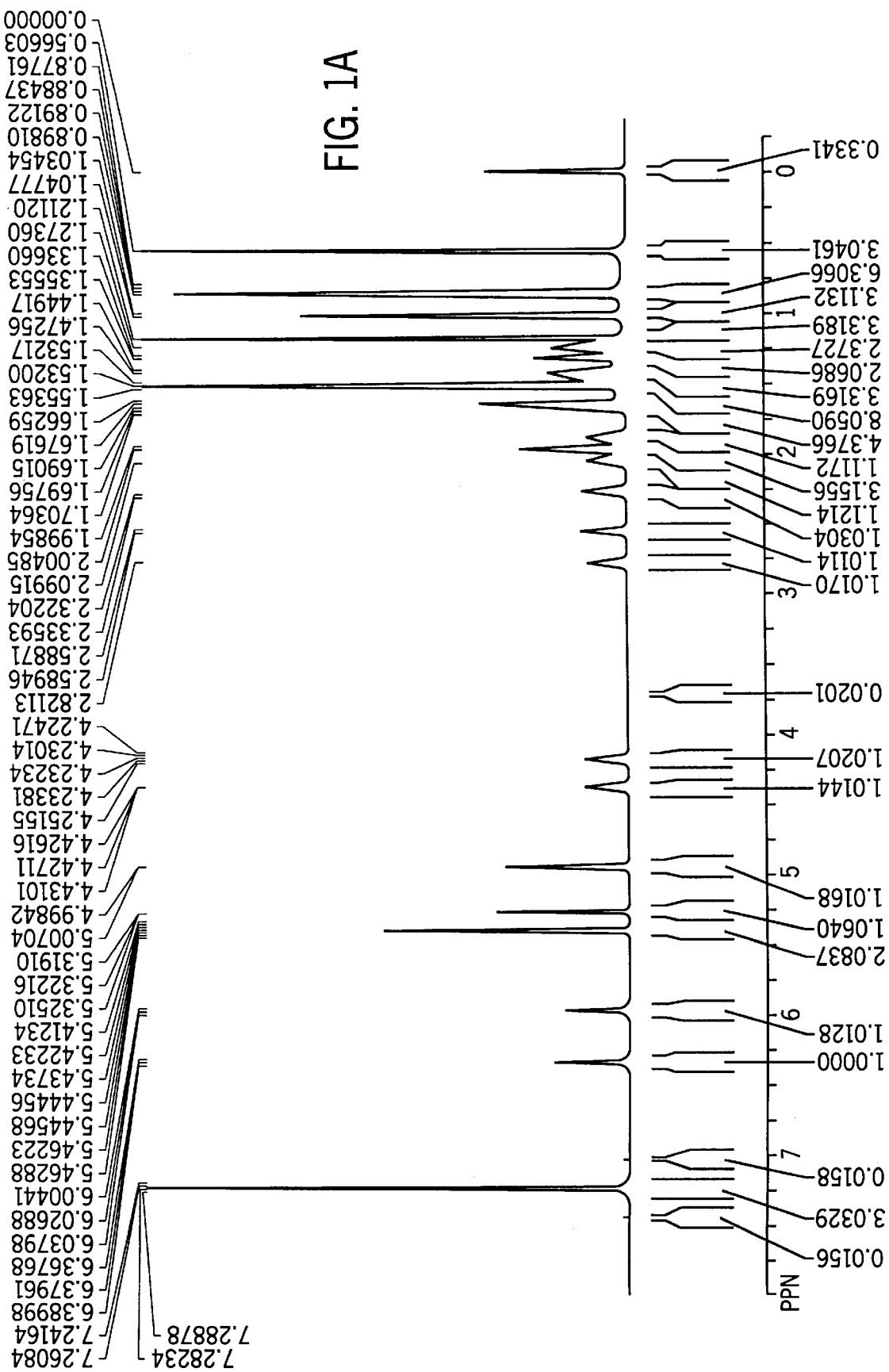
Figure 1B:
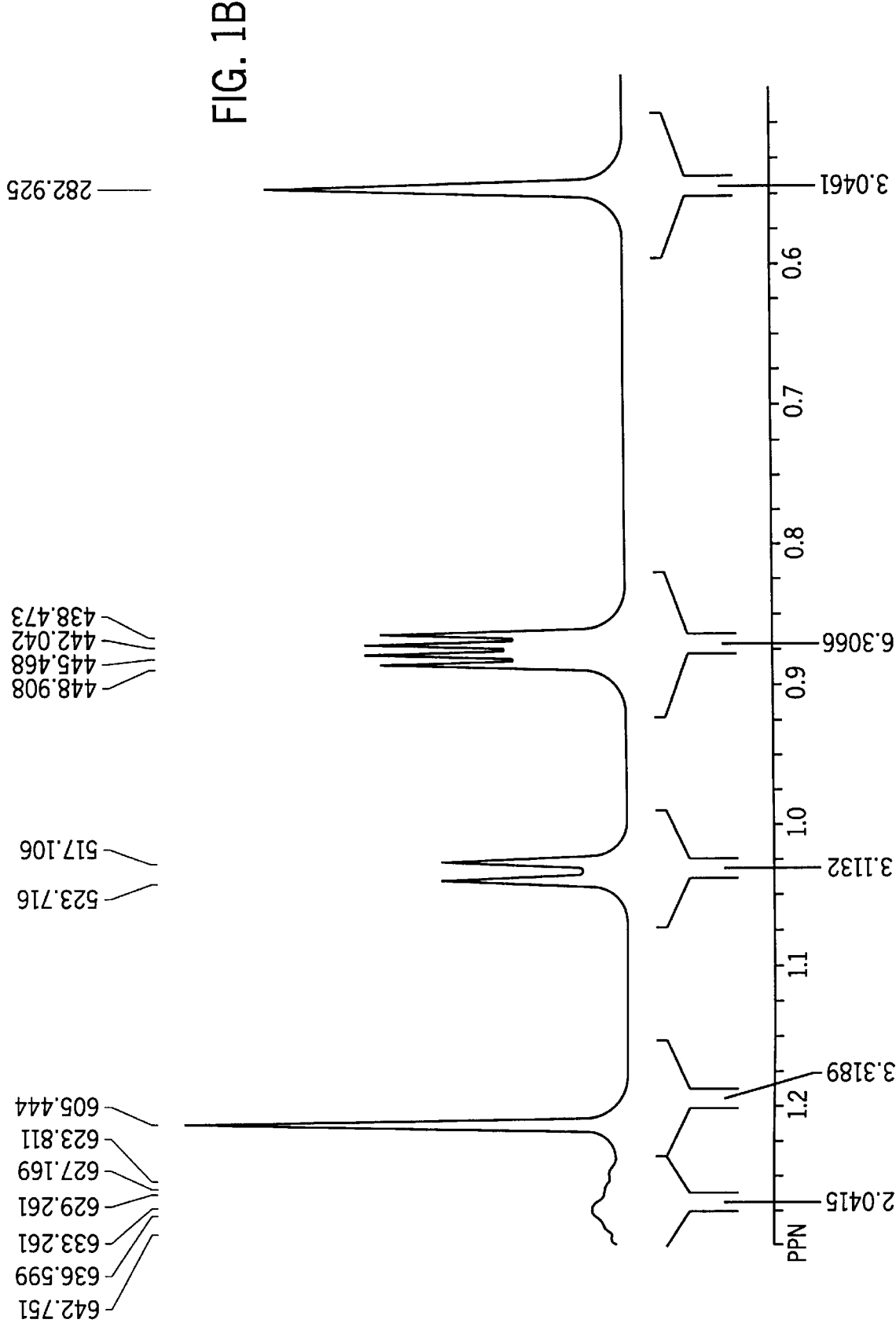
Figure 4A:
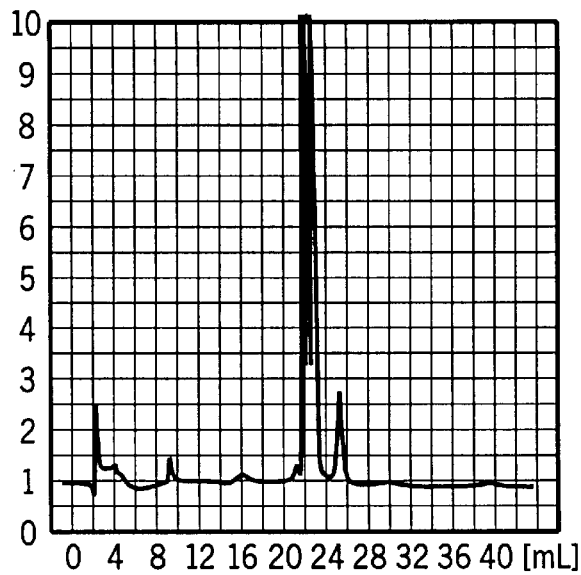
FIGS. 4a–4d are HPLC (4.6 mm×25 cm Zorbax-Eclipse XDB-C18 column, 20% water in methanol, 1 mL/min; UV detection at 260 nm) profiles of the solid 1α,24(S)-dihydroxyvitamin $D_2$ material before crystallization (FIG. 4a) and the crystals resulted after two crystallizations using the following solvent systems: acetone-hexane (FIG. 4b), 2-propanol-hexane (FIG. 4c) and HCOOEt-petroleum ether (FIG. 4d). In the region indicated by asterisk (ca. 22 mL) sensitivity was decreased 20 times.
Figure 4B:
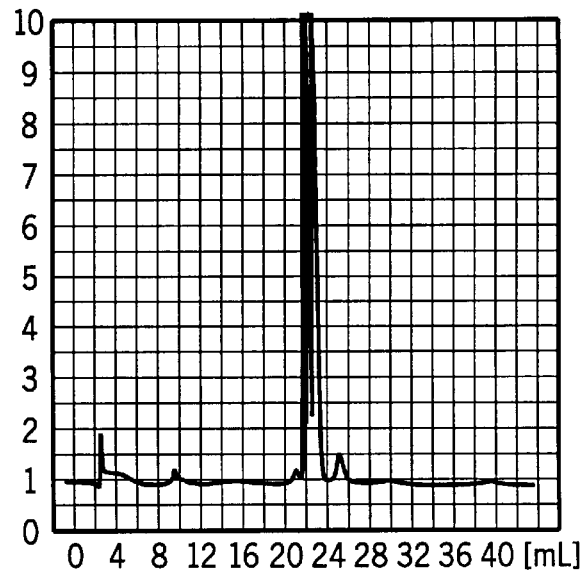
Figure 4C:
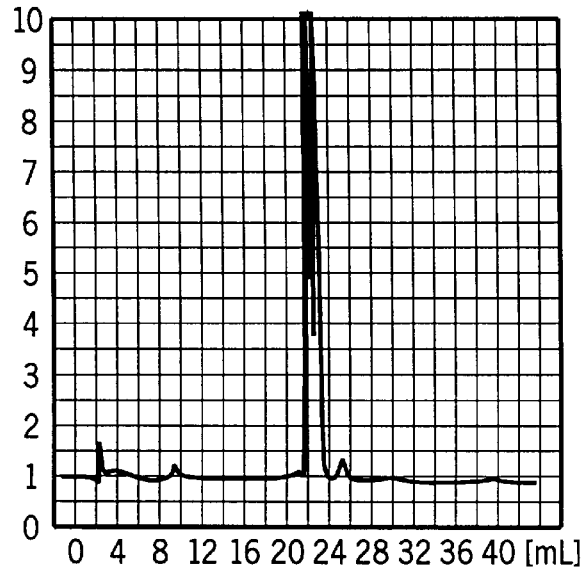
Figure 4D:
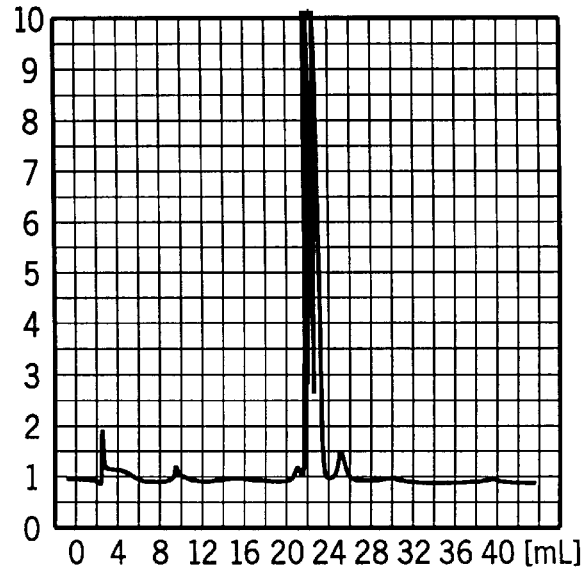
Figure 5A:
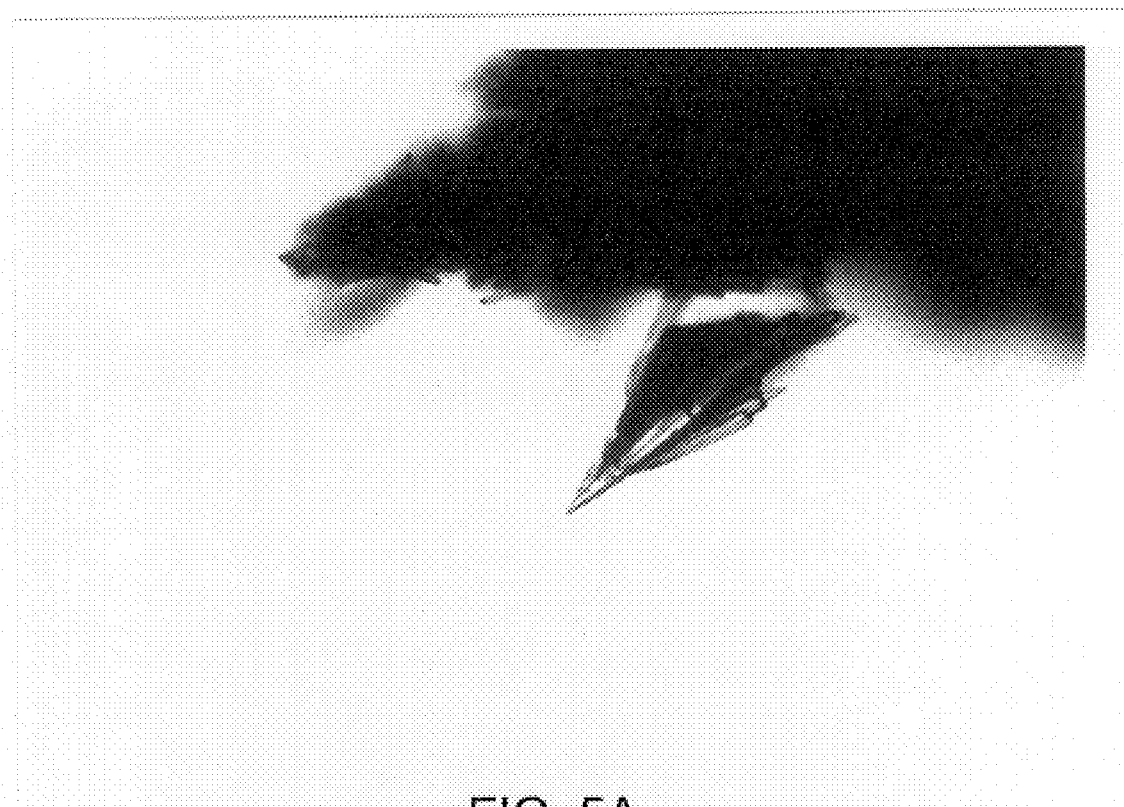
FIGS. 5a–5c are microscope-magnified images of the crystals of 1α,24(S)-dihydroxyvitamin $D_2$ resulted after two crystallizations from: acetone-hexane (FIG. 5a), 2-propanol-hexane (FIG. 5b) and HCOOEt-petroleum ether (FIG. 5c).
Figure 5B:
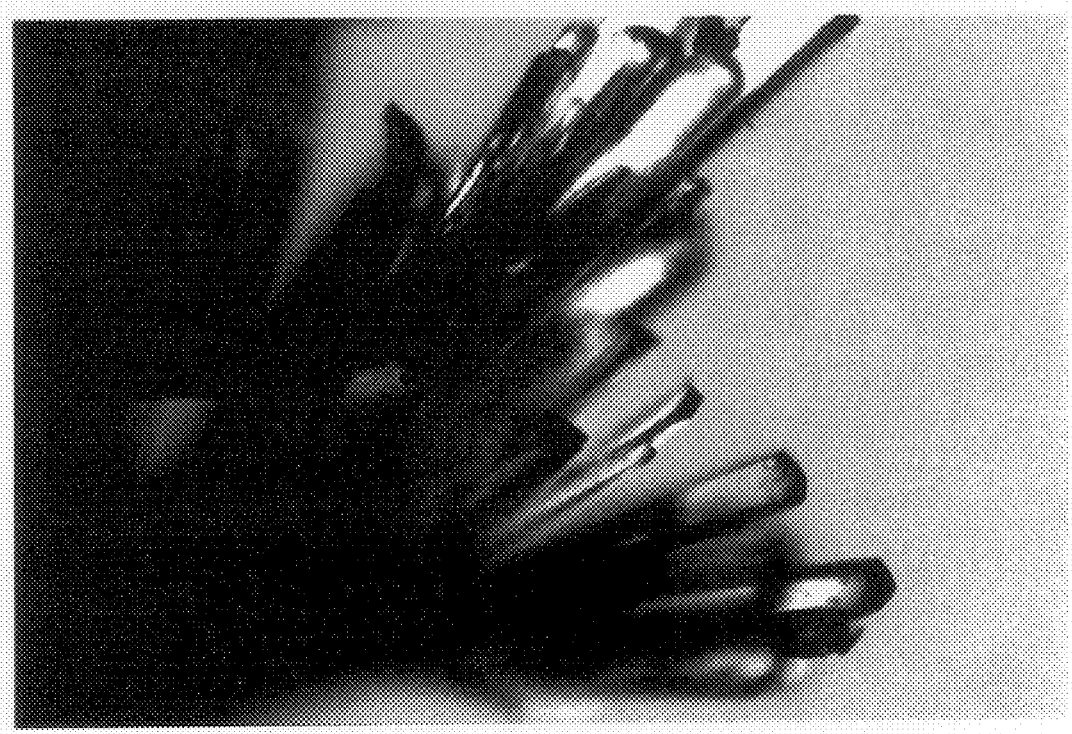
Figure 5C:
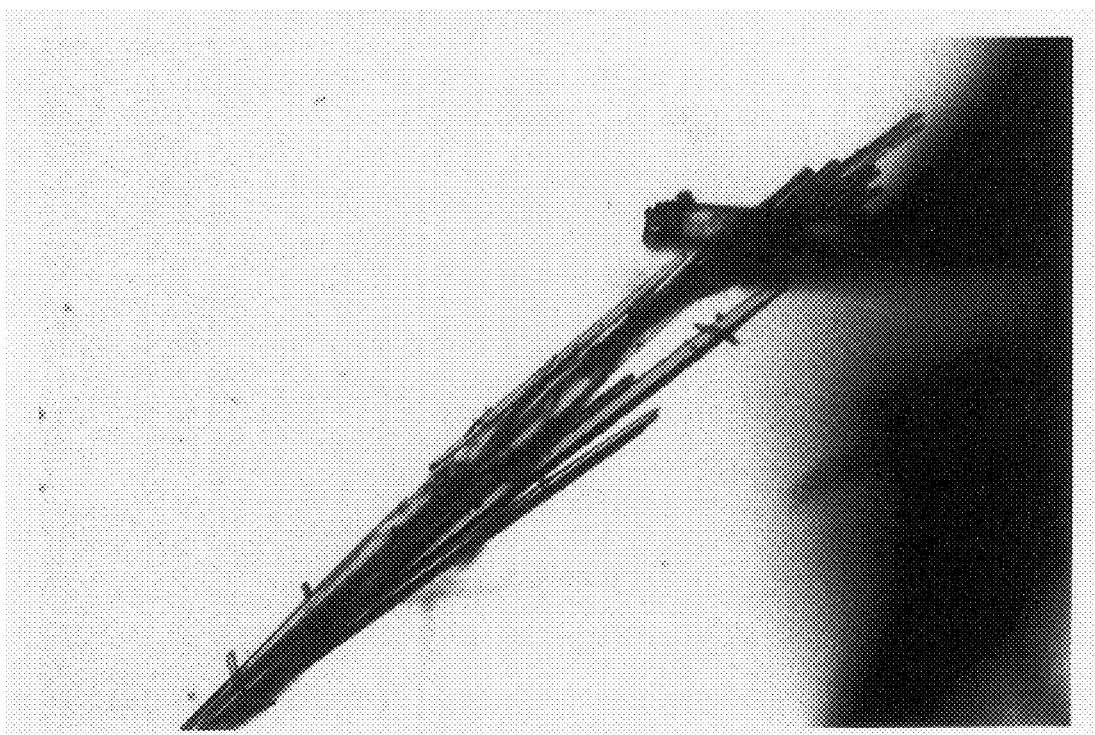
Figure 6:
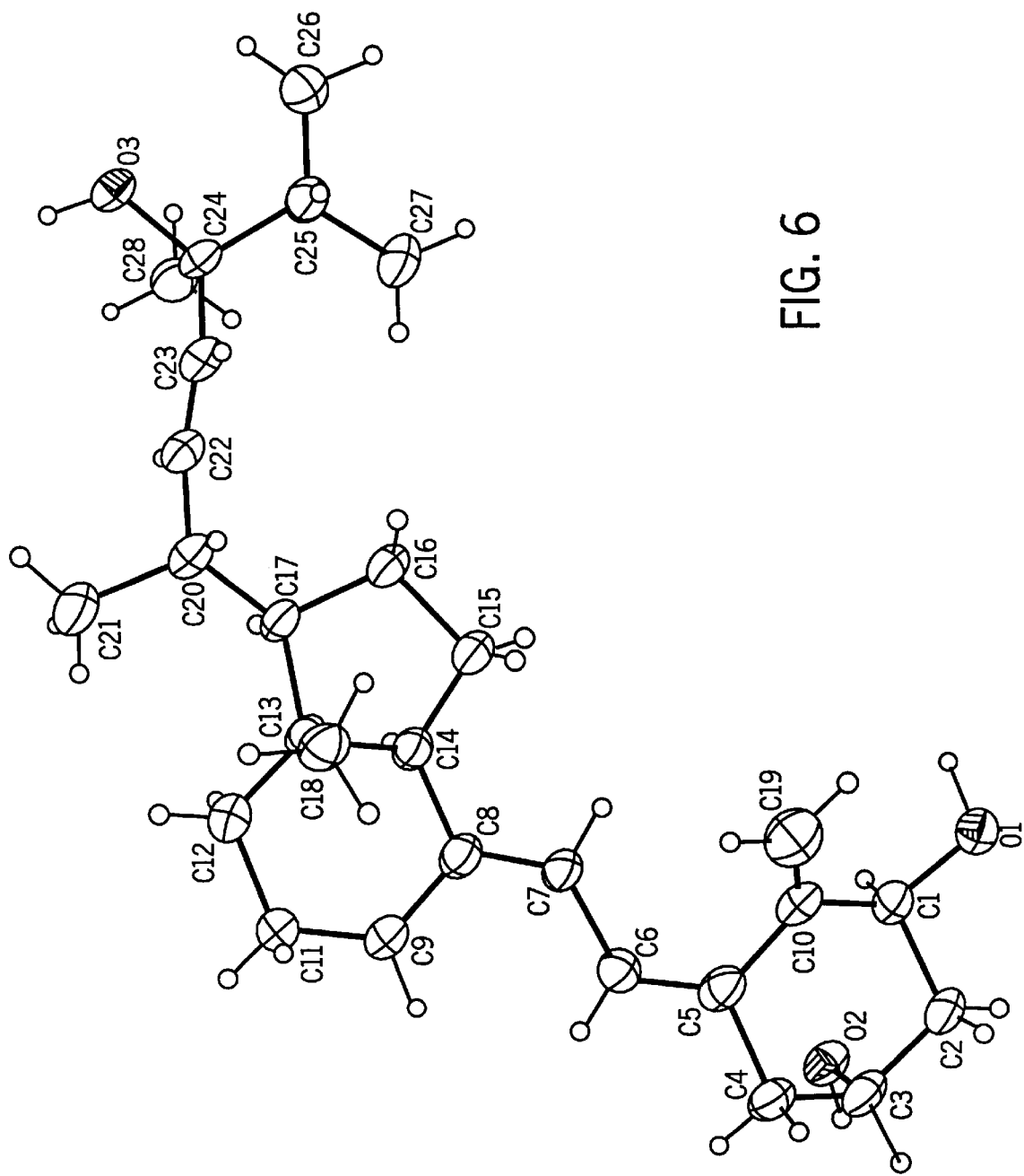
FIG. 6 is an illustration of the three dimensional structure of 1α,24(S)-dihydroxyvitamin $D_2$ as defined by the atomic positional parameters discovered and set forth herein.

The usefulness and advantages of the present crystallization procedures is shown in the following specific Examples. Solid 1α,24(S)-dihydroxyvitamin $D_2$ product which was purified by chromatography on silica and was used as a suitable starting material. This material showed reasonably good 500 MHz $^1$H NMR spectrum (FIGS. 1a, 1b), but concomitant compounds were detected by straight- and reverse-phase HPLC (FIGS. 2a and 4a, respectively) and, moreover, the presence of some oxidation products was confirmed by TLC (presence of the spot of $R_f$ 0). After recrystallization from the solvents listed above, the precipitated material was observed under microscope to confirm its crystalline form (FIGS. 5a–5c). Additionally, in the case of crystals precipitated from 2-propanol-hexane, X-ray diffraction analysis was performed (FIG. 6). The corresponding crops of crystals were then carefully analyzed and their significantly improved purity was confirmed by straight-phase HPLC (FIGS. 2b, 2c, 2d), reverse-phase HPLC (FIGS. 4b, 4c, 4d), TLC and 500 MHz $^1$H NMR (FIGS. 1c–1h). Yields of crystallizations were high and the obtained crystals showed a relatively sharp melting point.

The corresponding straight- and reverse-phase HPLC profiles of the recrystallized 1α,24(S)-dihydroxyvitamin $D_2$, shown in FIGS. 2b–2d and 4b–4d, respectively, clearly indicate a considerable improvement in the compound purity. The important observation consists of the significantly diminished proportion of the concomitant 1α,24(R)-dihydroxyvitamin $D_2$ (peak of retention time ca. 30 mL on FIGS. 2b–2d and ca. 25 mL on FIGS. 4b–4d) in the recrystallized compound; content of this R-isomer impurity has decreased more than 3 times (3.3–5.3) in respect to its value in the starting 1α,24(S)-dihydroxyvitamin $D_2$ product and does not exceed 0.5%.

The described crystallization process of the synthetic 1α,24(S)-dihydroxyvitamin $D_2$ product represents a valuable purification method, which can remove products derived from the synthetic path, including its concomitant 24-epimeric compound, namely, 1α,24(R)-dihydroxyvitamin $D_2$. Such impurity is a result of the nonstereospecific construction of the side chain (U.S. Pat. No. 5,786,348 and 5,789,397). In such case the separation of both epimeric vitamins is necessary and it is usually performed during the last stage of the synthesis. However, column chromatography and straight-phase separation of the 24-epimers is practically impossible due to their similar chromatographical properties, and larger-scale separation is also difficult by reverse-phase HPLC.

CRYSTALLIZATION OF 1α,24-DIHYDROXYVITAMIN $D_2$

EXAMPLE 1

Figure 3A:
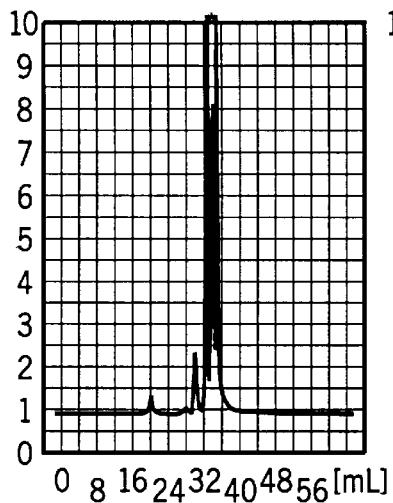
FIGS. 3a–3i are HPLC (10 mm×25 cm Zorbax-Sil column, 20% 2-propanol in hexane, 4 mL/min; UV detection at 260 nm) profiles of the crystals of 1α,24(S)-dihydroxyvitamin $D_2$ resulted after single crystallization using the following solvent systems: acetone-hexane (FIG. 3a), 2-propanol-hexane (FIG. 3d) and HCOOEt-petroleum ether (FIG. 3g); the HPLC profiles of mother liquors after single crystallization using the following solvent systems: acetone-hexane (FIG. 3b); 2-propanol-hexane (FIG. 3e) and HCOOEt-petroleum ether (FIG. 3h); and the HPLC profiles of mother liquors after two crystallizations using the following solvent systems: acetone-hexane (FIG. 3c); 2-propanol-hexane (FIG. 3f) and HCOOEt-petroleum ether (FIG. 3i). Region with decreased sensitivity (ca. 34 mL) is indicated by asterisk.
Figure 3B:
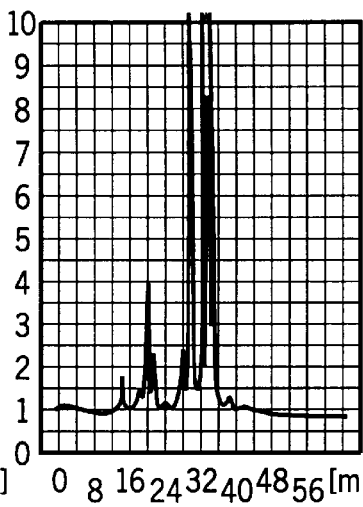

Crystallization from Acetone-hexane (a) 1α,24(S)-dihydroxyvitamin $D_2$ product (25 mg, m.p. 136–142.5° C.) was dissolved in boiling acetone (0.18 mL, Fisher Scientific) under argon atmosphere and hexane (0.72 mL, Burdick & Jackson) was added. The solution was left at room temperature (68° F.) for a few hours and then in a refrigerator (35–45° F.) overnight. The precipitated crystals were filtered off, washed with a small volume of a cold hexane and dried. The yield of crystalline material was 15 mg (60%). HPLC profiles of crystals and mother liquor are shown in FIGS. 3a, 3b.

Figure 2A:
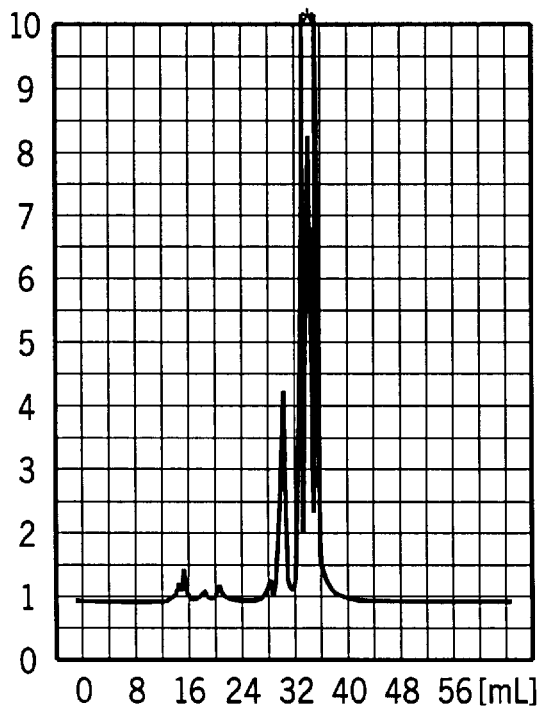
FIGS. 2*a*–2*d* are HPLC (10 mm×25 cm Zorbax-Sil column, 20% 2-propanol in hexane, 4 mL/min; UV detection at 260 nm) profiles of the solid 1α,24(S)-dihydroxyvitamin $D_2$ material before crystallization (FIG. 2*a*) and the crystals resulted after two crystallizations using the following solvent systems: acetone-hexane (FIG. 2b), 2-propanol-hexane (FIG. 2c) and HCOOEt-petroleum ether (FIG. 2d). In the region indicated by asterisk (ca. 34 mL) sensitivity was decreased 20 times.
Figure 2B:
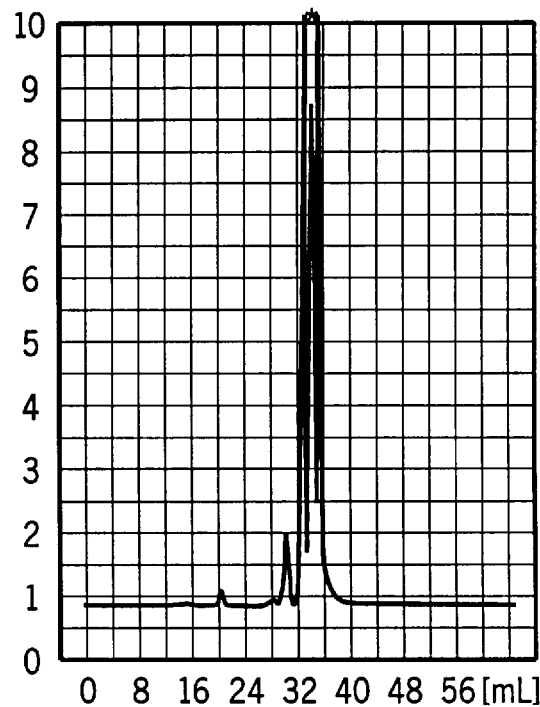
Figure 3C:
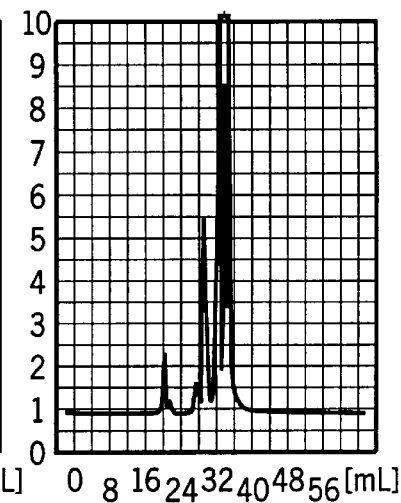

(b) These crystals of 1α,24(S)-dihydroxyvitamin $D_2$ (12 mg) were recrystallized from acetone (0.07 mL) and hexane (0.3 mL) as described in Example 1(a) and the precipitated crystals (9 mg, 75%), m.p. 146.5–151° C. were observed under a microscope (FIG. 5a) and analyzed by straight-phase HPLC (crystals: FIG. 2b; mother liquors: FIG. 3c), reverse-phase HPLC (FIG. 4b) and $^1$H NMR (FIGS. 1c, 1d).

Figure 3D:
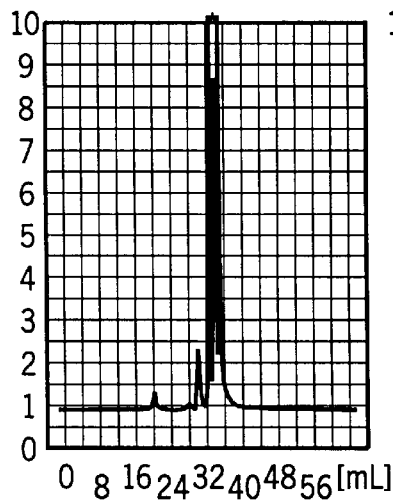
Figure 3E:
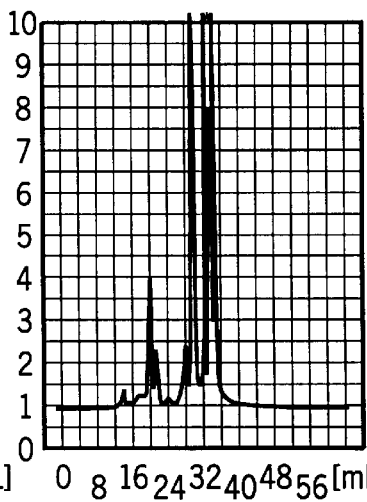

EXAMPLE 2
Crystallization from 2-propanol-hexane (a) 1α,24(S)-dihydroxyvitamin $D_2$ product (25 mg) was dissolved in a boiling 2-propanol-hexane mixture (1:4, 0.75 mL; Burdick & Jackson) under argon atmosphere, left at room temperature (68° F.) for a few hours and then in a refrigerator (35–45° F.) overnight. The precipitated crystals were filtered off, washed with a small volume of a cold hexane and dried. The yield of crystalline material was 17 mg (68%) HPLC profiles of crystals and mother liquor are shown in FIGS. 3d, 3e.

Figure 1E:
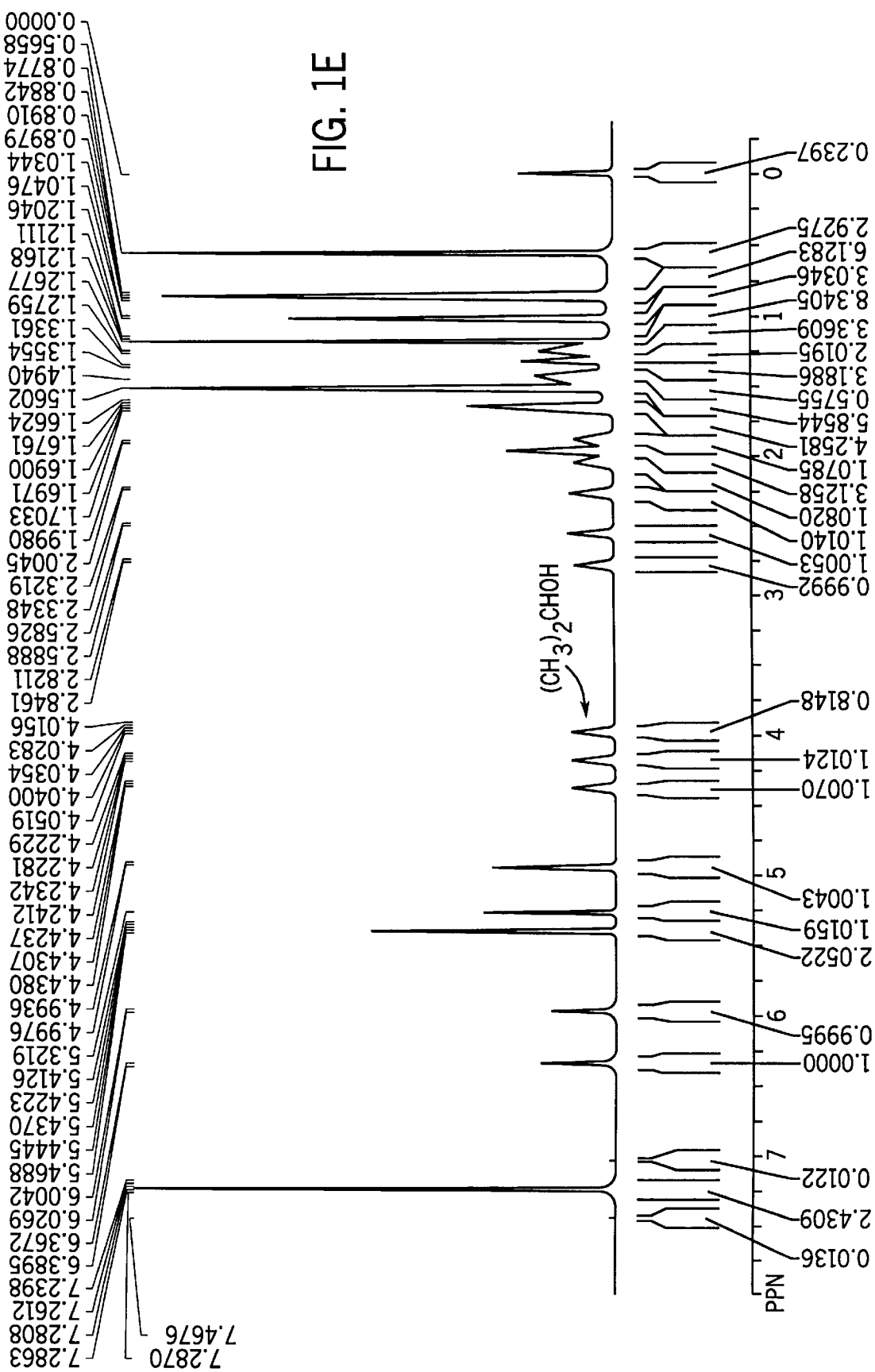
Figure 1F:
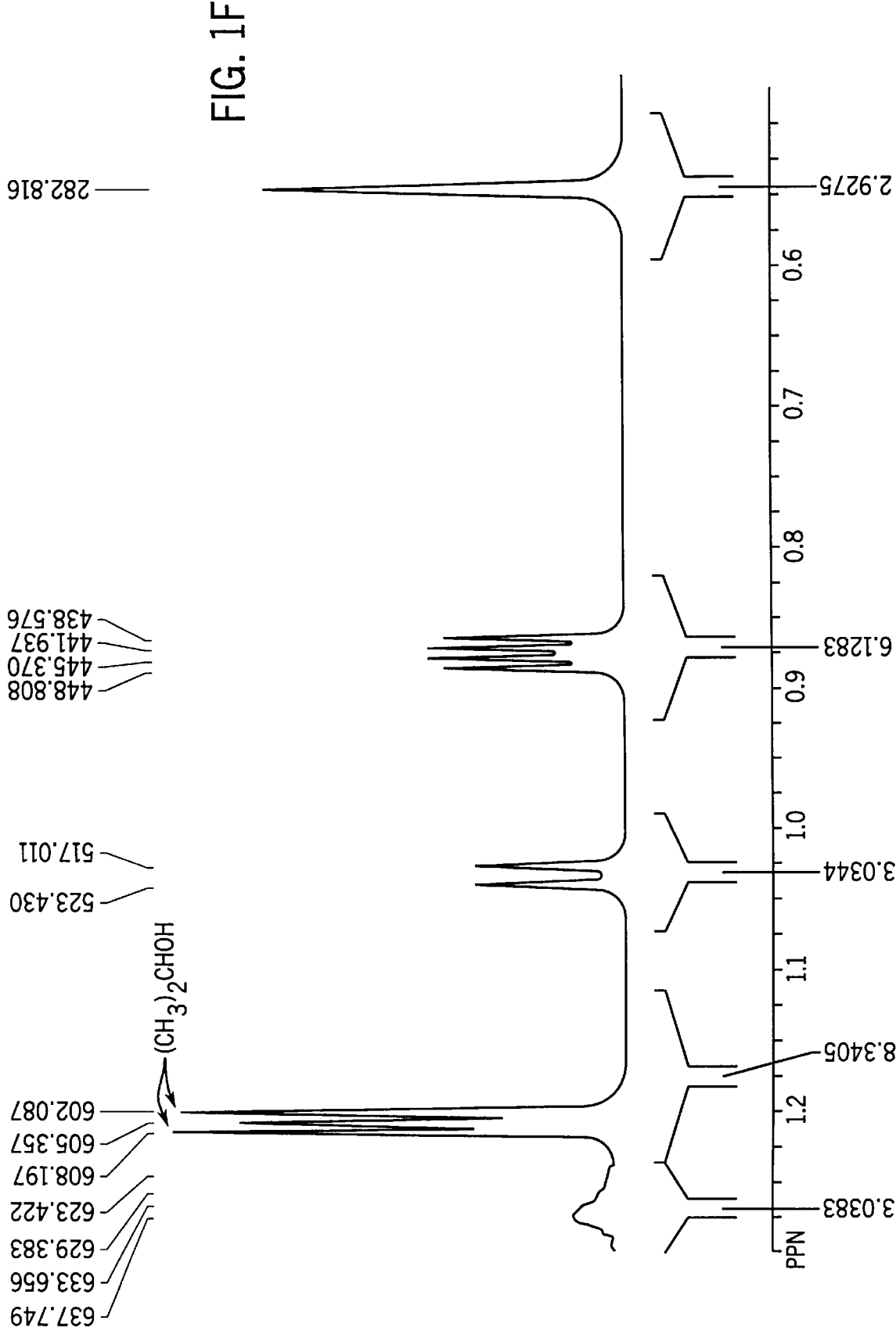
Figure 2C:
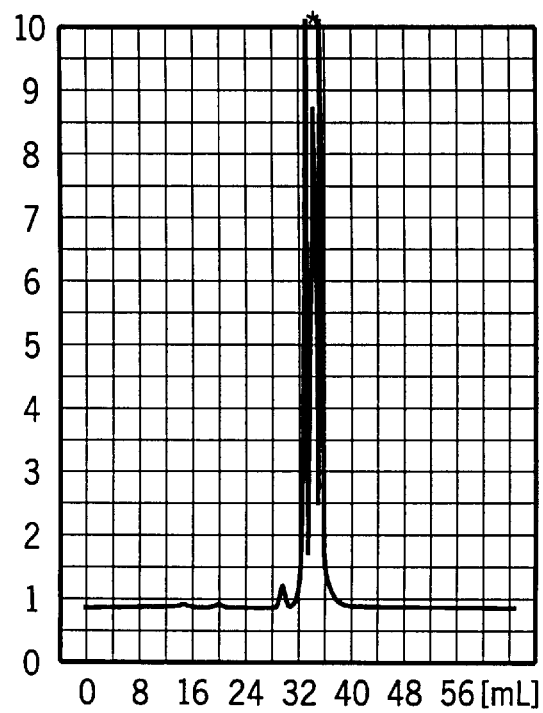
Figure 3F:
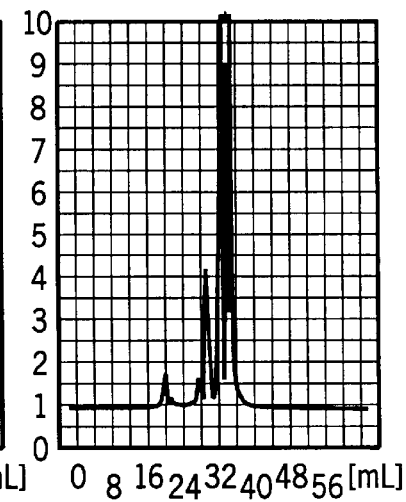

(b) These crystals of 1α,24(S)-dihydroxyvitamin $D_2$ product (15 mg) were recrystallized from 2-propanol-hexane mixture (1:4, 0.43 mL) as described in Example 2(a) and the precipitated crystals (8 mg, 53%) m.p. 147–151.5° C., were observed under a microscope (FIG. 5b) and analyzed by straight-phase HPLC (crystals: FIG. 2c; mother liquors: FIG. 3f), reverse-phase HPLC (FIG. 4c) and $^1$H NMR (FIGS. 1e, 1f).

Figure 3G:
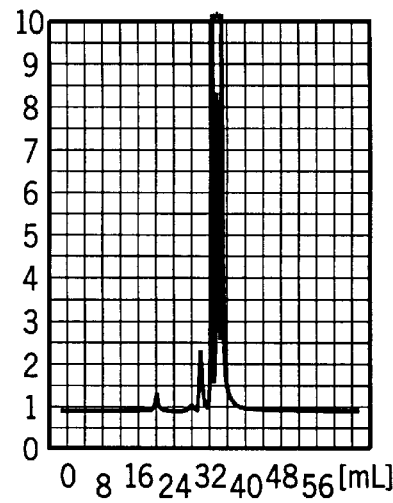
Figure 3H:
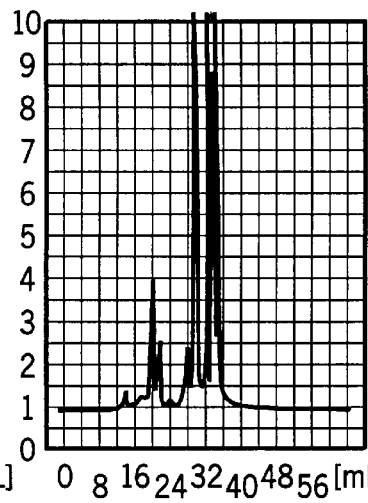

EXAMPLE 3
Crystallization from Ethyl Formate-petroleum Ether (a) 1α,24(S)-dihydroxyvitamin $D_2$ product (25 mg) was dissolved in boiling ethyl formate (0.5 mL, Aldrich) under argon atmosphere and petroleum ether (1 mL, b.p. 35–60° C.; Aldrich) was added. The solution was left at room temperature (68° F.) for a few hours and then in a refrigerator (35–45° F.) overnight. The precipitated crystals were filtered off, washed with a small volume of a cold hexane and dried. The yield of crystalline material was 17 mg (68%). HPLC profiles of crystals and mother liquor are shown in FIGS. 3g, 3h.

Figure 1G:
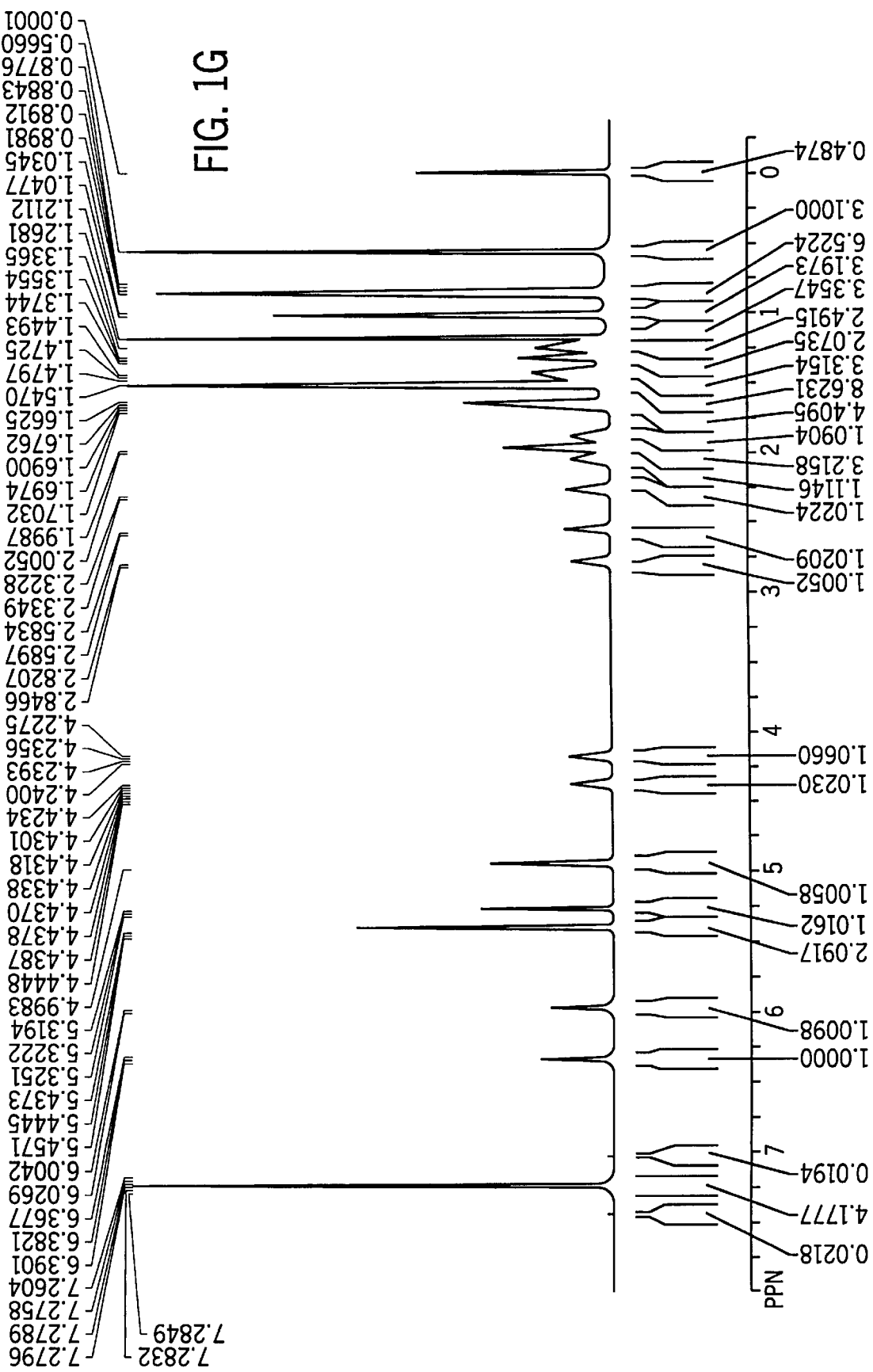
Figure 2D:
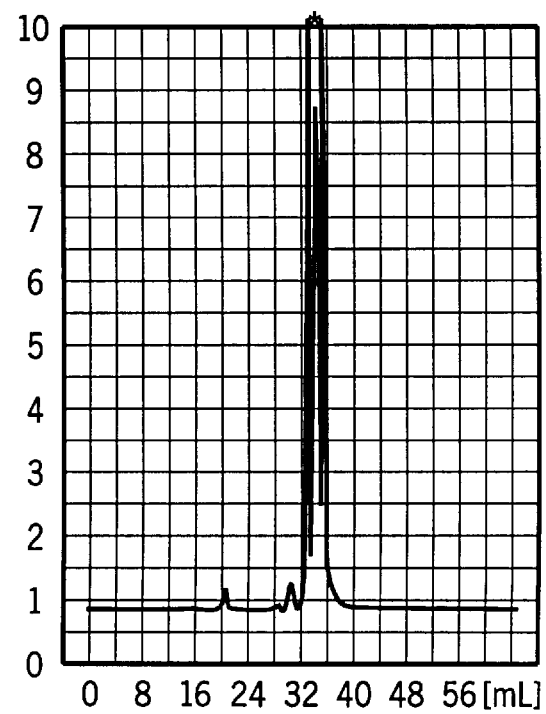
Figure 3I:
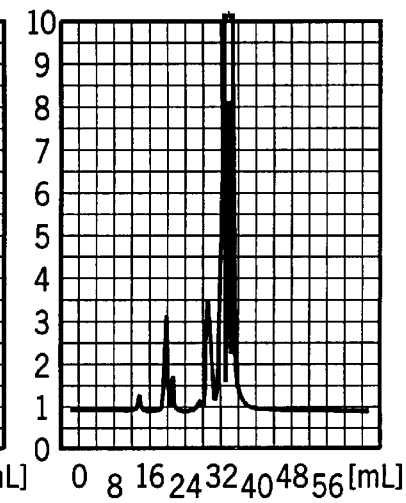

(b) These crystals of 1α,24(S)-dihydroxyvitamin $D_2$ (15 mg) were recrystallized from ethyl formate (0.25 mL) and petroleum ether (0.5 mL) as described in Example 3(a) and the precipitated crystals (9 mg, 60%), m.p. 142–146.5° C., were observed under a microscope (FIG. 5c) and analyzed by straight-phase HPLC (crystals: FIG. 2d; mother liquors, FIG. 3i), reverse-phase HPLC (FIG. 4d) and $^1$H NMR (FIGS. 1g, 1h).

Experimental

A colorless prism-shaped crystal of dimensions 0.42× 0.17×0.08 mm was selected for structural analysis. Intensity data for this compound were collected using a Bruker SMART ccd area detector, (a) Data collection: SMART Software Reference Manual (1994). Bruker-AXS, 6300 Enterprise Dr., Madison, Wis. 53719–1173, U.S.A., (b) Data Reduction: SAINT Software Reference Manual (1995). Brunker-AXS, 6300 Enterprise Drive, Madison, Wis. 53719–1173, U.S.A., mounted on a Bruker Platform goniometer using graphite-monochromated Mo Kγ radiation (λ=0.71073 Å). The sample was cooled to 133K. The intensity data, which nominally covered one and a half hemispheres of reciprocal space, were measured as a series of ω oscillation frames each of 0.3° for 90 sec/frame. The detector was operated in 512×512 mode and was positioned 5.00 cm from the sample. Coverage of unique data was 99.9% complete to 25.00 degrees in θ. Cell parameters were determined from a non-linear least squares fit of 5435 peaks in the range 2.30<θ<28.28°. The first 50 frames were repeated at the end of data collection and yielded 156 peaks showing a variation of 0.01% during the data collection. A total of 9896 data were measured in the range 1.61<θ<28.30°. The data were corrected for absorption by the empirical method G. M. Sheldrick (1996). SADABS. Program for Empirical Absorption Correction of Area Detector Data. University of Göttingen, Germany, giving minimum and maximum transmission factors of 0.769 and 0.970. The data were merged to form a set of 7019 independent data with R(int)=0.0389.

The monoclinic space group P2(1) was determined by systematic absences and statistical tests and verified by subsequent refinement. The structure was solved by direct methods and refined by full-matrix least-squares methods on $F^2$, (a) G.M. Sheldrick (1994). SHELXTL Version 5 Reference Manual, Bruker-AXS, 6300 Enterprise Drive, Madison, Wis. 53719–1173, U.S.A. (b) International Tables for Crystallography, Vol. C, Tables 6.1.1.4, 4.2.6.8, and 4.2.4.2, Kluwer: Boston (1995). Hydrogen atom positions were initially determined by geometry and refined by a riding model. Non-hydrogen atoms were refined with anisotropic displacement parameters. A total of 353 parameters were refined against 7 restraints and 7019 data to give wR($F^2$)=0.1274 and S=0.952 for weights of w=1/[$\sigma^2$ ($F^2$)+ (0.0670 P)$^2$], where P=[$F_o^2$+2$F_c^2$]/3. The final R(F) was 0.0504 for the 5187 observed, [F>4σ(F)], data. The largest shift/s.u. was 0.006 in the final refinement cycle. The final difference map had maxima and minima of 0.241 and −0.155 e/Å$^3$, respectively. The absolute structure was determined by refinement of the Flack parameter, H. D. Flack, Acta Cryst. A39, 876–881 (1983). The polar axis restraints were taken from Flack and Schwarzenbach, H. D. Flack and D. Schwarzenback, Acta Cryst. A44, 499–506 (1988).

The displacement ellipsoids are drawn at the 50% probability level in FIG. 6. The solvent molecule of 2-propanol was disordered and modeled in two orientations with occupancies of 0.473(10) and 0.527(10) for the unprimed and primed atoms (not shown in FIG. 6). Restraints on the positional parameters of the solvent were required for the refinement to achieve convergence.

The three dimensional structure of 1α,24(S)-dihydroxyvitamin $D_2$ as defined by the following physical data and atomic positional parameters described and calculated herein is illustrated in FIG. 6.

TABLE 1

Crystal data and structure refinement for 1α,24(S)-dihydroxyvitamin $D_2$.

| Empirical formula | (C28 H44 O3) | |
| --- | --- | --- |
|  | (C3 H8 O) | |
| Formula weight | 488.73 | |
| Crystal system | Monoclinic | |
| Space group | P2(1) | |
| Unit cell dimensions | a = 12.8196(11) Å | α = 90° |
|  | b = 7.6363(6) Å | β = 99.270(2)° |
|  | c = 15.4915(13) Å | γ = 90° |
| Volume | 1496.7(2) Å$^3$ | |
| Z | 2 | |
| Density (calculated) | 1.084 Mg/m$^3$ | |
| Wavelength | 0.71073 Å | |
| Temperature | 133(2) K. | |
| F(000) | 540 | |
| Absorption coefficient | 0.069 mm$^{-1}$ | |
| Absorption correction | Empirical | |
| Max. and min. transmission | 0.970 and 0.769 | |

TABLE 1-continued

Crystal data and structure refinement for 1α,24(S)-dihydroxyvitamin $D_2$.

| | |
|---|---|
| Theta range for data collection | 1.61 to 28.300. |
| Reflections collected | 9896 |
| Independent reflections | 7019 [R(int) = 0.0389] |
| Data/restraints/parameters | 7019/7(disorder)/353 |
| wR($F^2$ all data) | wR2 = 0.1274 |
| R(F obsd data) | R1 = 0.0504 |
| Goodness-of-fit on $F^2$ | 0.952 |
| Observed data [I > 2v(I)] | 5187 |
| Absolute structure parameter | −1.3(11) |
| Largest and mean shift/s.u. | 0.006 and 0.000 |
| Largest diff. peak and hole | 0.241 and −0.155 e/Å$^3$ |

TABLE 2

Atomic coordinates and equivalent isotropic displacement parameters for 1α,24(S)-dihydroxyvitamin $D_2$. U(eq) is defined as one third of the trace of the orthogonalized $U_{ij}$ tensor.

| | x | y | z | U(eq) |
|---|---|---|---|---|
| O(1) | 0.74103(14) | 0.26699(19) | 0.64786(9) | 0.0504(4) |
| O(2) | 0.71159(11) | 0.81818(19) | 0.65629(8) | 0.0398(3) |
| O(3) | 0.71370(12) | 0.0537(2) | −0.21338(9) | 0.0422(4) |
| C(1) | 0.75494(16) | 0.4442(3) | 0.62449(12) | 0.0340(4) |
| C(2) | 0.78823(16) | 0.5444(3) | 0.70961(11) | 0.0358(4) |
| C(3) | 0.80863(15) | 0.7362(3) | 0.69351(12) | 0.0347(4) |
| C(4) | 0.88914(16) | 0.7581(3) | 0.63196(12) | 0.0377(5) |
| C(5) | 0.85897(14) | 0.6546(3) | 0.54858(12) | 0.0332(4) |
| C(6) | 0.85205(15) | 0.7322(3) | 0.47018(12) | 0.0363(4) |
| C(7) | 0.82031(15) | 0.6503(3) | 0.38543(12) | 0.0351(4) |
| C(8) | 0.81345(15) | 0.7288(3) | 0.30735(12) | 0.0355(4) |
| C(9) | 0.83815(19) | 0.9172(3) | 0.29164(13) | 0.0438(5) |
| C(10) | 0.83535(15) | 0.4674(3) | 0.56360(12) | 0.0332(4) |
| C(11) | 0.90937(19) | 0.9379(3) | 0.22164(13) | 0.0439(5) |
| C(12) | 0.86813(17) | 0.8370(3) | 0.13713(12) | 0.0381(5) |
| C(13) | 0.85111(14) | 0.6444(3) | 0.15568(11) | 0.0302(4) |
| C(14) | 0.77427(15) | 0.6343(3) | 0.22337(12) | 0.0332(4) |
| C(15) | 0.74419(18) | 0.4419(3) | 0.22396(13) | 0.0426(5) |
| C(16) | 0.73673(17) | 0.3872(3) | 0.12732(12) | 0.0386(5) |
| C(17) | 0.78577(14) | 0.5385(3) | 0.07984(11) | 0.0310(4) |
| C(18) | 0.95630(15) | 0.5526(3) | 0.18950(13) | 0.0408(5) |
| C(19) | 0.88104(18) | 0.3357(3) | 0.52951(15) | 0.0485(6) |
| C(20) | 0.83816(16) | 0.4686(3) | 0.00427(12) | 0.0344(4) |
| C(21) | 0.89386(18) | 0.6079(3) | −0.04330(13) | 0.0431(5) |
| C(22) | 0.75293(16) | 0.3790(3) | −0.05931(12) | 0.0345(4) |
| C(23) | 0.74996(16) | 0.2140(3) | −0.08077(12) | 0.0352(4) |
| C(24) | 0.66492(16) | 0.1167(3) | −0.14141(12) | 0.0331(4) |
| C(28) | 0.57047(17) | 0.2288(3) | −0.17729(14) | 0.0428(5) |
| C(25) | 0.63467(17) | −0.0501(3) | −0.09445(13) | 0.0389(5) |
| C(26) | 0.5682(2) | −0.1799(3) | −0.15392(16) | 0.0490(6) |
| C(27) | 0.5808(2) | 0.0051(3) | −0.01633(15) | 0.0537(6) |
| O(1S) | 0.6790(4) | 0.0433(9) | 0.5132(5) | 0.0525(15) |
| C(1S) | 0.5785(5) | 0.0407(9) | 0.4589(4) | 0.0579(19) |
| C(2S) | 0.568(2) | 0.193(2) | 0.3972(15) | 0.082(6) |
| C(3S) | 0.5668(13) | −0.1295(19) | 0.4094(16) | 0.068(4) |
| O(1S') | 0.6310(6) | 0.0515(9) | 0.5266(3) | 0.0531(15) |
| C(1S') | 0.6298(6) | 0.0414(9) | 0.4348(3) | 0.0622(19) |
| C(2S') | 0.589(2) | 0.216(2) | 0.4011(14) | 0.091(5) |
| C(3S') | 0.5714(16) | −0.117(2) | 0.3957(17) | 0.104(8) |

TABLE 3

Bond lengths [Å] and angles [°] for 1α,24(S)-dihydroxyvitamin $D_2$.

| | | | |
|---|---|---|---|
| O(1)-C(1) | 1.419(2) | C(13)-C(17) | 1.556(2) |
| O(2)-C(3) | 1.429(2) | C(14)-C(15) | 1.519(3) |
| O(3)-C(24) | 1.446(2) | C(15)-C(16) | 1.542(3) |
| C(1)-C(10) | 1.516(3) | C(16)-C(17) | 1.556(3) |
| C(1)-C(2) | 1.525(3) | C(17)-C(20) | 1.536(3) |
| C(2)-C(3) | 1.515(3) | C(20)-C(22) | 1.512(3) |
| C(3)-C(4) | 1.523(3) | C(20)-C(21) | 1.534(3) |
| C(4)-C(5) | 1.511(3) | C(22)-C(23) | 1.303(3) |
| C(5)-C(6) | 1.341(3) | C(23)-C(24) | 1.514(3) |
| C(5)-C(10) | 1.487(3) | C(24)-C(28) | 1.514(3) |
| C(6)-C(7) | 1.452(3) | C(24)-C(25) | 1.547(3) |
| C(7)-C(8) | 1.340(3) | C(25)-C(26) | 1.518(3) |
| C(8)-C(9) | 1.501(3) | C(25)-C(27) | 1.526(3) |
| C(8)-C(14) | 1.502(3) | O(1S)-C(1S) | 1.421(5) |
| C(9)-C(11) | 1.534(3) | C(1S)-C(2S) | 1.500(6) |
| C(10)-C(19) | 1.317(3) | C(1S)-C(3S) | 1.504(6) |
| C(11)-C(12) | 1.537(3) | O(1S')-C(1S') | 1.422(5) |
| C(12)-C(13) | 1.521(3) | C(1S')-C(2S') | 1.498(6) |
| C(13)-C(18) | 1.535(3) | C(1S')-C(3S') | 1.501(6) |
| C(13)-C(14) | 1.552(3) | | |
| O(1)-C(1)-C(10) | 113.37(16) | C(8)-C(9)-C(11) | 112.23(18) |
| O(1)-C(1)-C(2) | 106.70(15) | C(19)-C(10)-C(5) | 123.8(2) |
| C(10)-C(1)-C(2) | 110.83(16) | C(19)-C(10)-C(1) | 123.4(2) |
| C(3)-C(2)-C(1) | 112.00(15) | C(5)-C(10)-C(1) | 112.72(16) |
| O(2)-C(3)-C(2) | 109.14(16) | C(9)-C(11)-C(12) | 112.84(17) |
| O(2)-C(3)-C(4) | 109.44(16) | C(13)-C(12)-C(11) | 111.33(16) |
| C(2)-C(3)-C(4) | 111.21(17) | C(12)-C(13)-C(18) | 111.18(17) |
| C(5)-C(4)-C(3) | 111.82(16) | C(12)-C(13)-C(14) | 107.58(16) |
| C(6)-C(5)-C(10) | 125.50(18) | C(18)-C(13)-C(14) | 111.39(15) |
| C(6)-C(5)-C(4) | 120.90(19) | C(12)-C(13)-C(17) | 115.88(15) |
| C(10)-C(5)-C(4) | 113.57(17) | C(18)-C(13)-C(17) | 110.89(16) |
| C(5)-C(6)-C(7) | 126.6(2) | C(14)-C(13)-C(17) | 99.28(14) |
| C(8)-C(7)-C(6) | 126.2(2) | C(8)-C(14)-C(15) | 120.64(17) |
| C(7)-C(8)-C(9) | 126.19(18) | C(8)-C(14)-C(13) | 113.65(15) |
| C(7)-C(8)-C(14) | 122.04(19) | C(15)-C(14)-C(13) | 103.99(16) |
| C(9)-C(8)-C(14) | 111.73(17) | C(14)-C(15)-C(16) | 103.42(17) |
| C(15)-C(16)-C(17) | 106.93(16) | O(3)-C(24)-C(25) | 105.13(15) |
| C(20)-C(17)-C(13) | 120.53(15) | C(28)-C(24)-C(25) | 113.08(18) |
| C(20)-C(17)-C(16) | 111.23(17) | C(23)-C(24)-C(25) | 108.79(16) |
| C(13)-C(17)-C(16) | 103.81(14) | C(26)-C(25)-C(27) | 110.29(18) |
| C(22)-C(20)-C(21) | 110.13(16) | C(26)-C(25)-C(24) | 114.26(17) |
| C(22)-C(20)-C(17) | 107.15(15) | C(27)-C(25)-C(24) | 111.56(18) |
| C(21)-C(20)-C(17) | 114.81(17) | O(1S)-C(1S)-C(2S) | 110.1(12) |
| C(23)-C(22)-C(20) | 126.32(19) | O(1S)-C(1S)-C(3S) | 108.7(8) |
| C(22)-C(23)-C(24) | 128.42(19) | C(2S)-C(1S)-C(3S) | 110.9(15) |
| O(3)-C(24)-C(28) | 108.95(16) | O(1S')-C(1S')-C(2S') | 104.3(9) |
| O(3)-C(24)-C(23) | 106.50(15) | O(1S')-C(1S')-C(3S') | 111.8(12) |
| C(28)-C(24)-C(23) | 113.83(17) | C(2S')-C(1S')-C(3S') | 117.1(14) |

TABLE 4

Anisotropic displacement parameters (Å$^2$ × 10$^3$) for 1α,24(S)-dihydroxyvitamin $D_2$. The anisotropic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| O(1) | 84(1) | 39(1) | 30(1) | 0(1) | 15(1) | −10(1) |
| O(2) | 49(1) | 41(1) | 29(1) | −8(1) | 4(1) | 8(1) |
| O(3) | 61(1) | 40(1) | 31(1) | −8(1) | 22(1) | −2(1) |
| C(2) | 44(1) | 43(1) | 22(1) | 0(1) | 10(1) | 3(1) |
| C(3) | 44(1) | 40(1) | 21(1) | −7(1) | 4(1) | 1(1) |
| C(4) | 41(1) | 46(1) | 26(1) | −7(1) | 3(1) | −9(1) |
| C(5) | 28(1) | 47(1) | 25(1) | −7(1) | 7(1) | −3(1) |
| C(6) | 37(1) | 44(1) | 29(1) | −5(1) | 8(1) | −10(1) |
| C(7) | 35(1) | 47(1) | 25(1) | −4(1) | 9(1) | −10(1) |
| C(8) | 35(1) | 47(1) | 25(1) | −4(1) | 8(1) | −6(1) |
| C(9) | 59(1) | 46(1) | 28(1) | −8(1) | 9(1) | −6(1) |
| C(10) | 33(1) | 43(1) | 23(1) | −4(1) | 2(1) | 2(1) |
| C(11) | 60(1) | 40(1) | 32(1) | −3(1) | 10(1) | −14(1) |
| C(12) | 46(1) | 43(1) | 27(1) | 0(1) | 9(1) | −8(1) |
| C(13) | 30(1) | 40(1) | 21(1) | −1(1) | 6(1) | −5(1) |
| C(14) | 33(1) | 44(1) | 24(1) | −2(1) | 7(1) | −6(1) |
| C(15) | 49(1) | 54(1) | 25(1) | −5(1) | 8(1) | −20(1) |
| C(16) | 44(1) | 48(1) | 25(1) | −5(1) | 7(1) | −12(1) |
| C(17) | 32(1) | 39(1) | 22(1) | −3(1) | 4(1) | −2(1) |
| C(18) | 35(1) | 54(1) | 32(1) | −2(1) | 0(1) | 0(1) |
| C(19) | 49(1) | 57(1) | 40(1) | −8(1) | 9(1) | 6(1) |
| C(20) | 38(1) | 41(1) | 24(1) | −5(1) | 7(1) | 1(1) |
| C(21) | 47(1) | 54(1) | 31(1) | −5(1) | 15(1) | −5(1) |
| C(22) | 41(1) | 41(1) | 22(1) | −2(1) | 5(1) | 5(1) |
| C(23) | 37(1) | 43(1) | 26(1) | −1(1) | 9(1) | 3(1) |

TABLE 4-continued

Anisotropic displacement parameters (Å² × 10³) for 1α,24(S)-dihydroxyvitamin D₂. The anisotropic displacement factor exponent takes the form: $-2\pi^2[h^2a^{*2}U_{11} + \ldots + 2\,h\,k\,a^*\,b^*\,U_{12}]$

| | $U_{11}$ | $U_{22}$ | $U_{33}$ | $U_{23}$ | $U_{13}$ | $U_{12}$ |
|---|---|---|---|---|---|---|
| C(24) | 41(1) | 35(1) | 26(1) | −7(1) | 10(1) | 1(1) |
| C(28) | 47(1) | 45(1) | 35(1) | −5(1) | 1(1) | 3(1) |
| C(25) | 43(1) | 43(1) | 33(1) | 0(1) | 11(1) | 2(1) |
| C(26) | 60(1) | 43(1) | 48(1) | −7(1) | 20(1) | −9(1) |
| C(27) | 68(2) | 63(1) | 35(1) | −4(1) | 23(1) | −16(1) |
| O(1S) | 71(4) | 47(2) | 35(3) | 0(2) | −4(3) | −6(3) |
| C(1S) | 46(4) | 86(4) | 44(4) | 2(3) | 13(3) | 3(3) |
| C(2S) | 52(7) | 116(10) | 76(9) | 42(9) | 7(6) | 29(9) |
| C(3S) | 43(6) | 108(10) | 51(6) | −34(5) | −1(4) | −2(6) |
| O(1S') | 78(4) | 50(2) | 30(2) | 5(2) | 4(2) | 3(3) |
| C(1S') | 49(4) | 102(5) | 35(3) | −4(3) | 4(2) | 3(3) |
| C(2S') | 73(10) | 139(11) | 56(6) | 33(6) | −3(5) | −10(6) |
| C(3S') | 81(9) | 165(15) | 66(9) | −44(8) | 10(6) | −40(9) |

TABLE 5

Hydrogen coordinates and isotropic displacement parameters for 1α,24(S)-dihydroxyvitamin D₂.

| | x | y | z | U(eq) |
|---|---|---|---|---|
| H(1O) | 0.7154 | 0.2011 | 0.5980 | 0.060 |
| H(2O) | 0.6925 | 0.9129 | 0.6947 | 0.048 |
| H(3O) | 0.7209 | 0.1479 | −0.2497 | 0.051 |
| H(1) | 0.6854 | 0.4912 | 0.5950 | 0.041 |
| H(2A) | 0.7320 | 0.5346 | 0.7462 | 0.043 |
| H(2B) | 0.8532 | 0.4910 | 0.7422 | 0.043 |
| H(3) | 0.8363 | 0.7938 | 0.7506 | 0.042 |
| H(4A) | 0.8946 | 0.8837 | 0.6174 | 0.045 |
| H(4B) | 0.9593 | 0.7188 | 0.6619 | 0.045 |
| H(6) | 0.8697 | 0.8530 | 0.4701 | 0.044 |
| H(7) | 0.8027 | 0.5294 | 0.3853 | 0.042 |
| H(9A) | 0.8737 | 0.9699 | 0.3471 | 0.053 |
| H(9B) | 0.7713 | 0.9816 | 0.2730 | 0.053 |
| H(11A) | 0.9812 | 0.8955 | 0.2455 | 0.053 |
| H(11B) | 0.9148 | 1.0637 | 0.2076 | 0.053 |
| H(12A) | 0.8005 | 0.8892 | 0.1088 | 0.046 |
| H(12B) | 0.9196 | 0.8477 | 0.0961 | 0.046 |
| H(14) | 0.7088 | 0.6975 | 0.1962 | 0.040 |
| H(15A) | 0.6756 | 0.4260 | 0.2445 | 0.051 |
| H(15B) | 0.7990 | 0.3732 | 0.2619 | 0.051 |
| H(16A) | 0.6620 | 0.3686 | 0.1007 | 0.046 |
| H(16B) | 0.7761 | 0.2770 | 0.1227 | 0.046 |
| H(17) | 0.7260 | 0.6153 | 0.0532 | 0.037 |
| H(18A) | 1.0078 | 0.5807 | 0.1512 | 0.061 |
| H(18B) | 0.9452 | 0.4256 | 0.1899 | 0.061 |
| H(18C) | 0.9831 | 0.5928 | 0.2490 | 0.061 |
| H(19A) | 0.9324 | 0.3576 | 0.4929 | 0.058 |
| H(19B) | 0.8627 | 0.2186 | 0.5415 | 0.058 |
| H(20) | 0.8916 | 0.3785 | 0.0284 | 0.041 |
| H(21A) | 0.9193 | 0.5545 | −0.0935 | 0.065 |
| H(21B) | 0.9539 | 0.6561 | −0.0031 | 0.065 |
| H(21C) | 0.8440 | 0.7021 | −0.0636 | 0.065 |
| H(22) | 0.6960 | 0.4500 | −0.0862 | 0.041 |
| H(23) | 0.8088 | 0.1457 | −0.0550 | 0.042 |
| H(25A) | 0.7023 | −0.1109 | −0.0706 | 0.047 |
| H(26A) | 0.6064 | −0.2152 | −0.2010 | 0.074 |
| H(26B) | 0.5011 | −0.1250 | −0.1791 | 0.074 |
| H(26C) | 0.5543 | −0.2832 | −0.1200 | 0.074 |
| H(27A) | 0.6233 | 0.0815 | 0.0205 | 0.081 |
| H(27B) | 0.5739 | −0.1112 | 0.0179 | 0.081 |
| H(27C) | 0.5105 | 0.0434 | −0.0372 | 0.081 |
| H(28A) | 0.5940 | 0.3296 | −0.2083 | 0.064 |
| H(28B) | 0.5360 | 0.2701 | −0.1290 | 0.064 |
| H(28C) | 0.5202 | 0.1593 | −0.2178 | 0.064 |
| H(1S) | 0.6790 | −0.0276 | 0.5547 | 0.063 |
| H(1S1) | 0.5221 | 0.0487 | 0.4964 | 0.069 |
| H(2S1) | 0.5939 | 0.2994 | 0.4296 | 0.123 |
| H(2S2) | 0.4940 | 0.2087 | 0.3714 | 0.123 |
| H(2S3) | 0.6104 | 0.1727 | 0.3507 | 0.123 |
| H(3S1) | 0.6057 | −0.1162 | 0.3603 | 0.102 |
| H(3S2) | 0.4918 | −0.1495 | 0.3870 | 0.102 |
| H(3S3) | 0.5952 | −0.2295 | 0.4454 | 0.102 |
| H(1S') | 0.6602 | −0.0383 | 0.5507 | 0.064 |
| H(1S2) | 0.7047 | 0.0316 | 0.4246 | 0.075 |
| H(2S4) | 0.5199 | 0.2383 | 0.4191 | 0.136 |
| H(2S5) | 0.5804 | 0.2165 | 0.3371 | 0.136 |
| H(2S6) | 0.6385 | 0.3081 | 0.4247 | 0.136 |
| H(3S4) | 0.6045 | −0.2183 | 0.4284 | 0.156 |
| H(3S5) | 0.5751 | −0.1324 | 0.3334 | 0.156 |
| H(3S6) | 0.4973 | −0.1090 | 0.4037 | 0.156 |

TABLE 6

Torsion angles [°] for 1α,24(S)-dihydroxyvitamin D₂.

| | | | |
|---|---|---|---|
| O(1)-C(1)-C(2)-C(3) | 178.48(16) | C(12)-C(13)-C(14)-C(15) | 168.80(16) |
| C(10)-C(1)-C(2)-C(3) | 54.6(2) | C(18)-C(13)-C(14)-C(15) | −69.1(2) |
| C(1)-C(2)-C(3)-O(2) | 66.0(2) | C(17)-C(13)-C(14)-C(15) | 47.76(18) |
| C(1)-C(2)-C(3)-C(4) | −54.8(2) | C(8)-C(14)-C(15)-C(16) | −166.13(18) |
| O(2)-C(3)-C(4)-C(5) | −68.2(2) | C(13)-C(14)-C(15)-C(16) | −37.2(2) |
| C(2)-C(3)-C(4)-C(5) | 52.5(2) | C(14)-C(15)-C(16)-C(17) | 11.8(2) |
| C(3)-C(4)-C(5)-C(6) | 126.3(2) | C(12)-C(13)-C(17)-C(20) | 80.8(2) |
| C(3)-C(4)-C(5)-C(10) | −51.6(2) | C(18)-C(13)-C(17)-C(20) | 47.1(2) |
| C(10)-C(5)-C(6)-C(7) | 0.1(3) | C(14)-C(13)-C(17)-C(20) | −164.38(17) |
| C(4)-C(5)-C(6)-C(7) | −177.57(18) | C(12)-C(13)-C(17)-C(16) | −153.88(17) |
| C(5)-C(6)-C(7)-C(8) | 179.9(2) | C(18)-C(13)-C(17)-C(16) | 78.17(19) |
| C(6)-C(7)-C(8)-C(9) | 0.6(4) | C(14)-C(13)-C(17)-C(16) | −39.08(18) |
| C(6)-C(7)-C(8)-C(14) | −176.76(18) | C(15)-C(16)-C(17)-C(20) | 148.70(17) |
| C(7)-C(8)-C(9)-C(11) | 132.1(2) | C(15)-C(16)-C(17)-C(13) | 17.7(2) |
| C(14)-C(8)-C(9)-C(11) | −50.3(2) | C(13)-C(17)-C(20)-C(22) | −177.80(17) |
| C(6)-C(5)-C(10)-C(19) | 55.8(3) | C(16)-C(17)-C(20)-C(22) | 60.4(2) |
| C(4)-C(5)-C(10)-C(19) | −126.3(2) | C(13)-C(17)-C(20)-C(21) | −55.2(2) |
| | | C(16)-C(17)-C(20)-C(21) | −176.91(17) |

TABLE 6-continued

Torsion angles [°] for 1α,24(S)-dihydroxyvitamin $D_2$.

| | | | |
|---|---|---|---|
| C(6)-C(5)-C(10)-C(1) | −125.7(2) | C(21)-C(20)-C(22)-C(23) | 116.8(2) |
| C(4)-C(5)-C(10)-C(1) | 52.1(2) | C(17)-C(20)-C(22)-C(23) | −117.7(2) |
| O(1)-C(1)-C(10)-C(19) | 5.6(3) | C(20)-C(22)-C(23)-C(24) | 177.65(18) |
| C(2)-C(1)-C(10)-C(19) | 125.6(2) | C(22)-C(23)-C(24)-O(3) | 117.2(2) |
| O(1)-C(1)-C(10)-C(5) | −172.83(15) | C(22)-C(23)-C(24)-C(28) | −2.8(3) |
| C(2)-C(1)-C(10)-C(5) | 52.9(2) | C(22)-C(23)-C(24)-C(25) | −129.9(2) |
| C(8)-C(9)-C(11)-C(12) | 50.6(3) | O(3)-C(24)-C(25)-C(26) | 53.6(2) |
| C(9)-C(11)-C(12)-C(13) | −54.9(3) | C(28)-C(24)-C(25)-C(26) | 65.2(2) |
| C(11)-C(12)-C(13)-C(18) | −65.8(2) | C(23)-C(24)-C(25)-C(26) | −.167.32(18) |
| C(11)-C(12)-C(13)-C(14) | 56.4(2) | O(3)-C(24)-C(25)-C(27) | −179.52(17) |
| C(11)-C(12)-C(13)-C(17) | 166.37(17) | C(28)-C(24)-C(25)-C(27) | −60.8(2) |
| C(7)-C(8)-C(14)-C(15) | −2.1(3) | C(23)-C(24)-C(25)-C(27) | 66.7(2) |
| C(9)-C(8)-C(14)-C(15) | −179.81(19) | | |
| C(7)-C(8)-C(14)-C(13) | −126.6(2) | | |
| C(9)-C(8)-C(14)-C(13) | 55.7(2) | | |
| C(12)-C(13)-C(14)-C(8) | −58.2(2) | | |
| C(18)-C(13)-C(14)-C(8) | 63.9(2) | | |
| C(17)-C(13)-C(14)-C(8) | −179.21(17) | | |

TABLE 7

Hydrogen bonds for 1α,24(S)-dihydroxyvitamin $D_2$ [Å and °].

| D-H . . . A | d(D-H) | d(H . . . A) | d(D . . . A) | <(DHA) |
|---|---|---|---|---|
| O(1)-H(1O) . . . O(1S) | 0.94 | 1.79 | 2.714(7) | 169.7 |
| O(1)-H(1O) . . . O(1S') | 0.94 | 1.82 | 2.715(7) | 159.1 |
| O(2)-H(2O) . . . O(3)#1 | 0.99 | 1.77 | 2.7009(18) | 154.8 |
| O(3)-H(3O) . . . O(1)#2 | 0.93 | 1.88 | 2.764(2) | 158.0 |
| O(1S)-H(1S) . . . O(2)#3 | 0.84 | 1.96 | 2.783(7) | 167.7 |
| O(1S')-H(1S') . . . O(2)#3 | 0.84 | 1.99 | 2.759(6) | 151.7 |

Symmetry transformations used to generate equivalent atoms:
1 x, y + 1, z + 1
2 x, y, z − 1
3 x, y − 1, z

We claim:

1. A method of purifying 1α,24(S)-dihydroxyvitamin $D_2$, comprising the steps of:
    (a) crystallizing 1α,24(S)-dihydroxyvitamin $D_2$ from a solvent, said solvent is a binary system selected from the group consisting of a 2-propanol and hexane mixture, and an ethyl formate and petroleum ether mixture; and
    (b) recovering the crystallized 1α,24(S)-dihydroxyvitamin $D_2$.

2. The method of claim 1 wherein said solvent comprises 2-propanol and hexane, and prior to crystallizing the 1α,24-dihydroxyvitamin $D_2$, boiling a mixture of 2-propanol and hexane and dissolving a product containing 1α,24(S)-dihydroxyvitamin $D_2$ in said boiling mixture.

3. The method of claim 1 wherein said solvent comprises ethyl formate and petroleum ether, and prior to crystallizing the 1α,24-dihydroxyvitamin $D_2$, boiling said ethyl formate, dissolving a product containing 1α,24(S)-dihydroxyvitamin $D_2$ in said boiling ethyl formate, and thereafter adding said petroleum ether to said boiling ethyl formate containing said 1α,24(S)-dihydroxyvitamin $D_2$.

4. The method of claim 1 wherein the step of recovering comprises filtering.

5. The method of claim 1 wherein steps (a) and (b) are repeated using the recovered crystals from step (b).

6. A method of purifying 1α,24(S)-dihydroxyvitamin $D_2$, comprising the steps of:
    (a) boiling 2-propanol-hexane mixture under inert atmosphere;
    (b) dissolving a product containing 1α,24(S)-dihydroxyvitamin $D_2$ to be purified in said mixture to form a solution;
    (c) cooling said solution below ambient temperature for a sufficient amount of time to form a precipitate of 1α,24(S)-dihydroxyvitamin $D_2$ crystals, and
    (d) recovering the 1α,24(S)-dihydroxyvitamin $D_2$ crystals.

7. The method of claim 6 wherein said solution is allowed to cool to ambient temperature prior to cooling below ambient temperature.

8. The method of claim 6 wherein said inert atmosphere is an argon atmosphere.

9. The method of claim 6 wherein said solution is cooled to between about 35° F. to about 45° F.

10. The method of claim 6 wherein the step of recovering comprises filtering.

11. The method of claim 6 wherein steps (a) and (d) are repeated using the recovered crystals from step (d) as the product in step (b).

12. A method of purifying 1α,24(S)-dihydroxyvitamin $D_2$, comprising the steps of:
    (a) boiling ethyl formate under inert atmosphere;
    (b) dissolving a product containing 1α,24(S)-dihydroxyvitamin $D_2$ to be purified in said boiling ethyl formate to form a solution;
    (c) adding petroleum ether to said solution;
    (d) cooling said solution below ambient temperature for a sufficient amount of time to form a precipitate of 1α,24(S)-dihydroxyvitamin $D_2$ crystals; and
    (e) recovering the 1α,24(S)-dihydroxyvitamin $D_2$ crystals.

13. The method of claim 12 wherein said solution is allowed to cool to ambient temperature prior to cooling below ambient temperature.

14. The method of claim 12 wherein said inert atmosphere is an argon atmosphere.

15. The method of claim 12 wherein said solution is cooled to between about 35° F. to about 45° F.

16. The method claim 12 wherein the step of recovering comprises filtering.

17. The method of claim 12 wherein steps (a) through (e) are repeated using the recovered crystals from step (e) as the product in step (b).

* * * * *